(12) United States Patent
Piran et al.

(10) Patent No.: US 8,609,856 B2
(45) Date of Patent: Dec. 17, 2013

(54) CRYSTALLINE FORMS OF FEBUXOSTAT

(71) Applicant: Teva Pharmaceuticals Industries Ltd., Petach-Tikva (IL)

(72) Inventors: Maytal Piran, Rishon Le Zion (IL); Leonid Metsger, Beer Sheva (IL)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 0 days.

(21) Appl. No.: 13/782,932

(22) Filed: Mar. 1, 2013

(65) Prior Publication Data

US 2013/0178504 A1 Jul. 11, 2013

Related U.S. Application Data

(63) Continuation of application No. 12/813,091, filed on Jun. 10, 2010, now Pat. No. 8,415,481.

(60) Provisional application No. 61/235,481, filed on Aug. 20, 2009, provisional application No. 61/233,552, filed on Aug. 13, 2009, provisional application No. 61/222,583, filed on Jul. 2, 2009, provisional application No. 61/185,775, filed on Jun. 10, 2009.

(51) Int. Cl.
*C07D 277/56* (2006.01)
*A61K 31/426* (2006.01)

(52) U.S. Cl.
USPC .......................... 548/201; 514/365

(58) Field of Classification Search
None
See application file for complete search history.

(56) References Cited

FOREIGN PATENT DOCUMENTS

| CN | 101085761 A | 12/2007 |
|----|----|----|
| CN | 101139325 A | 3/2008 |
| CN | 101386605 A | 3/2009 |
| CN | 101412700 A | 4/2009 |
| CN | 101412700 A | 4/2009 |
| CN | 100546985 C | 10/2009 |
| CN | 101648926 A | 2/2010 |
| CN | 101671314 A | 3/2010 |
| CN | 101684107 A | 3/2010 |
| CN | 101684108 A | 3/2010 |
| CN | 101759656 A | 6/2010 |
| CN | 101768136 A | 7/2010 |
| CN | 101768150 | 7/2010 |
| CN | 101768150 A | 7/2010 |
| CN | 101805310 A | 8/2010 |
| CN | 101817801 A | 9/2010 |
| CN | 101858578 A | 10/2010 |
| CN | 101891702 A | 11/2010 |
| CN | 102093308 A | 6/2011 |
| CN | 102093309 A | 6/2011 |
| EP | 1 020 454 A1 | 12/1999 |
| EP | 1 020 454 A1 | 7/2000 |
| EP | 1 488 790 A1 | 12/2004 |
| EP | 2 039 691 A1 | 12/2007 |
| EP | 2 039 691 A1 | 3/2009 |
| JP | 2003-261548 | 9/2003 |
| JP | 2003-261548 A | 9/2003 |
| WO | WO 92/09279 A1 | 6/1992 |
| WO | WO 99/65885 A1 | 12/1999 |
| WO | WO 03/082279 A1 | 10/2003 |
| WO | WO 2008/067773 A1 | 6/2008 |
| WO | WO 2008067773 | 6/2008 |
| WO | WO 2012/048861 A1 | 4/2012 |

OTHER PUBLICATIONS

Hasegawa, M., "A Facile One-Pot Synthesis of a 4-Alkoxy-1,3 Benzenedicarbonitrile," Heterocycles, vol. 47, No. 2, p. 857-864, (1998).
Kitamura, M. et al, "Effects of Solvent Compositions and Temperature on Polymorphism and Crystallization Behavior of Thiazole-Derivative," Journal of Crystal Growth, vol. 235, p. 676-686 (2002).
Bavin, M. *Polymorphism in Process Development, Chemistry & Industry* dated Aug. 21, 1989.
Brittain, H. *Polymorphism in Pharmaceutical Solids, Discovery Laboratories, Inc.* dated Dec. 31, 2006.
Byrn, S. et al. *Pharmaceutical Solids: A Strategic Approach to Regulatory Considerations, Pharmaceutical Research*, vol. 12, No. 7, 1995.
Opposition to European Patent Ep 2 398 784 B1 (*Teva Pharmaceutical Industries Ltd.*, IL) dated Jul. 17, 2013.
Notice of Opposition to a European Patent corresponding to EP 2398784 dated Jul. 17, 2013.
*European Pharmacopoeia 7.0 Monographs ANX3* dated Jan. 2008.
*European Pharmacopoeia 7.0 Power Flow ANX2* dated Jan. 2010.
*Glossary* Byrn et al. ANX1.
Hilfiker, R. et al. *Polymorphism in the Pharmaceutical Industry.* Wiley-VCH Verlag GmbH & Co.
Kitamura, M., et al. *Effects of Solvent Composition and Temperature on Polymorphism and Crystallization Behavior of Thiazole-Derviative. Journal of Crystal Growth* 236 (2002) 676-686, dated Dec. 12, 2001.
Kitamura, M. *Controlling Factors and Mechanism of Polymorphic Crystallization. Department of Chemical Engineering.* Dated Jul. 7, 2004.
Kitamura, M. *Effects of Temperature on Antisolvent Crystallization and Transformation Behaviros of Thiazole-Derivative Polymorphs. Department of Mechanical and System Engineering*, dated Nov. 30, 2005.
Opposition to EP 2 398 784 81, Annex 4. *Solubility test of different febuxostat polymorphs.*

*Primary Examiner* — Nyeemah A Grazier
(74) *Attorney, Agent, or Firm* — Woodcock Washburn LLP

(57) ABSTRACT

New forms of Febuxostat have been prepared and characterized. These forms are useful, for example, in the chronic management of hyperuricemia in patients with gout.

20 Claims, 31 Drawing Sheets

CRYSTALLINE FORMS OF FEBUXOSTAT

CROSS-REFERENCED TO RELATED APPLICATIONS

This application is a continuation of U.S. patent application Ser. No. 12/813,091, filed Jun. 10, 2010 which is based upon and claims priority to U.S. Provisional Patent Application Nos. 61/235,481, filed Aug. 20, 2009; 61/233,552, filed Aug. 13, 2009; 61/222,583, filed Jul. 2, 2009; and 61/185,775, filed Jun. 10, 2009 all of which the disclosure is hereby incorporated in its entirety by reference.

FIELD OF INVENTION

The present invention encompasses crystalline forms of 2-(3-cyano-4-isobutyloxyphenyl)-4-methylthiazole-5-carboxylic acid.

BACKGROUND OF THE INVENTION

Febuxostat, 2-(3-cyano-4-isobutyloxyphenyl)-4-methylthiazole-5-carboxylic acid, having the following formula:

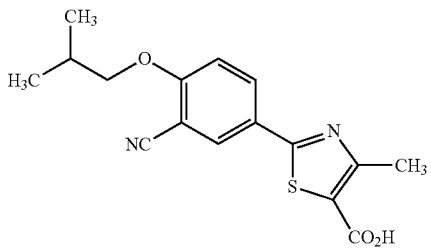 [SMILES: Cc1nc(-c2ccc(OCC(C)C)c(C#N)c2)sc1C(=O)O]

is a xanthine oxidase (XO) inhibitor indicated for the chronic management of hyperuricemia in patients with gout. Febuxostat is not recommended for the treatment of asymptomatic hyperuricemia. Febuxostat is administrated in the form of tablets that are marketed in the USA and the EU under the name ULORIC®.

PCT publication no. WO 1992/109279 describes Febuxostat. PCT publication no. WO 1999/065885, PCT publication no. WO 2003/082279, PCT publication no. WO 2008/067773, CN 100546985, CN 101139325, CN101085761, CN 101412700, CN 101386605, CN101648926, CN 101671314, CN 101684107 and *Hetrocycles*, 47, 2, 857-864 describe crystalline forms of Febuxostat including forms A, B, C, D, G, H, I, J, K and M, as well as an amorphous form.

The present invention relates to the solid state physical properties of Febuxostat, 2-[3-cyano-4-(2-methylpropoxy)phenyl]-4-methylthiazole-5-carboxylic acid. These properties can be influenced by controlling the conditions under which 2-[3-cyano-4-(2-methylpropoxy) phenyl]-4-methylthiazole-5-carboxylic acid is obtained in solid form.

Polmorphism, the occurrence of different crystal forms, is a property of some molecules and molecular complexes. A single molecule may give rise to a variety of polymorphs having distinct crystal structures and physical properties like melting point, thermal behaviours (e.g. measured by thermogravimetric analysis—"TGA", or differential scanning calorimetry—"DSC"), X-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms. New polymorphic forms and solvates of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Febuxostat.

SUMMARY OF THE INVENTION

In one embodiment, the present invention encompasses crystalline Febuxostat, designated as form F1. Form F1 can be characterized by data selected from: a powder XRD pattern with peaks at 5.8°, 6.8°, 8.1°, 11.8° and 17.4°±0.2° 2θ; an XRPD pattern substantially as depicted in FIG. 1; a solid-state $^{13}$C NMR spectrum with signals at 123.8, 163.1 and 168.5±0.2 ppm; a solid-state $^{13}$C NMR spectrum having chemical shift differences between the signal exhibiting the lowest chemical shift and another in the chemical shift range of 100 to 180 ppm of 23.4, 62.7 and 68.1±0.1 ppm; a solid-state $^{13}$C NMR spectrum substantially as depicted in FIG. 2 or 3; and combinations thereof.

In another embodiment, the present invention encompasses crystalline Febuxostat, designated as form F2, Form F2 can be characterized by data selected from: a powder XRD pattern with peaks at 3.0°, 5.9°, 8.8°, 11.8° and 12.5°±0.2° 2θ; an XRPD pattern substantially as depicted in FIG. 4 or FIG. 5; a solid-state $^{13}$C NMR spectrum with signals at 112.3, 163.9, 168.8±0.2 ppm; a solid-state $^{13}$C NMR spectrum having chemical shifts differences between the signal exhibiting the lowest chemical shift and another in the chemical shift range of 100 to 180 ppm of 11.5, 63.1 and 68.0±0.1 ppm; a solid-state $^{13}$C NMR spectrum substantially as depicted in FIG. 6 or 7; and combinations thereof.

In yet another embodiment, the present invention encompasses crystalline Febuxostat, designated as Form F10. Form F10 can be characterized by data selected from: an X-ray powder diffraction pattern having peaks at 6.7°, 7.7°, 12.8°, 13.3° and 20.0°±0.2° 2θ; an X-ray powder diffraction pattern substantially as depicted in FIG. 8; a solid state $^{13}$C NMR spectrum with signals at 112.7, 125.7, 132.4 and 168.3±0.2 ppm; a solid-state $^{13}$C NMR spectrum having chemical shifts differences between the signal exhibiting the lowest chemical shift and another in the chemical shift range of 100 to 180 ppm of 11.7, 24.7, 31.4 and 67.3±0.1 ppm; a solid-state $^{13}$C NMR spectrum substantially as depicted in FIG. 9 or 10; and combinations thereof.

In one embodiment, the present invention provides a pharmaceutical composition comprising any one, or combination, of the Febuxostat crystalline Forms described above and at least one pharmaceutically acceptable excipient.

In another embodiment, the present invention provides the use of any one of the above pharmaceutical compositions for the treatment of hyperuricemia in patients with gout. In another embodiment, the invention provides a method of treating hyperuricemia in patients with gout, comprising administering a therapeutically effective amount of at lease one of the above pharmaceutical compositions to a patient with gout. In another embodiment, the invention provides the use of any one of the forms of Febuxostat described above in the manufacture of a medicament fro the treatment of hyperuricemia in patients with gout.

DETAILED DESCRIPTION OF THE INVENTION

Figure 1:
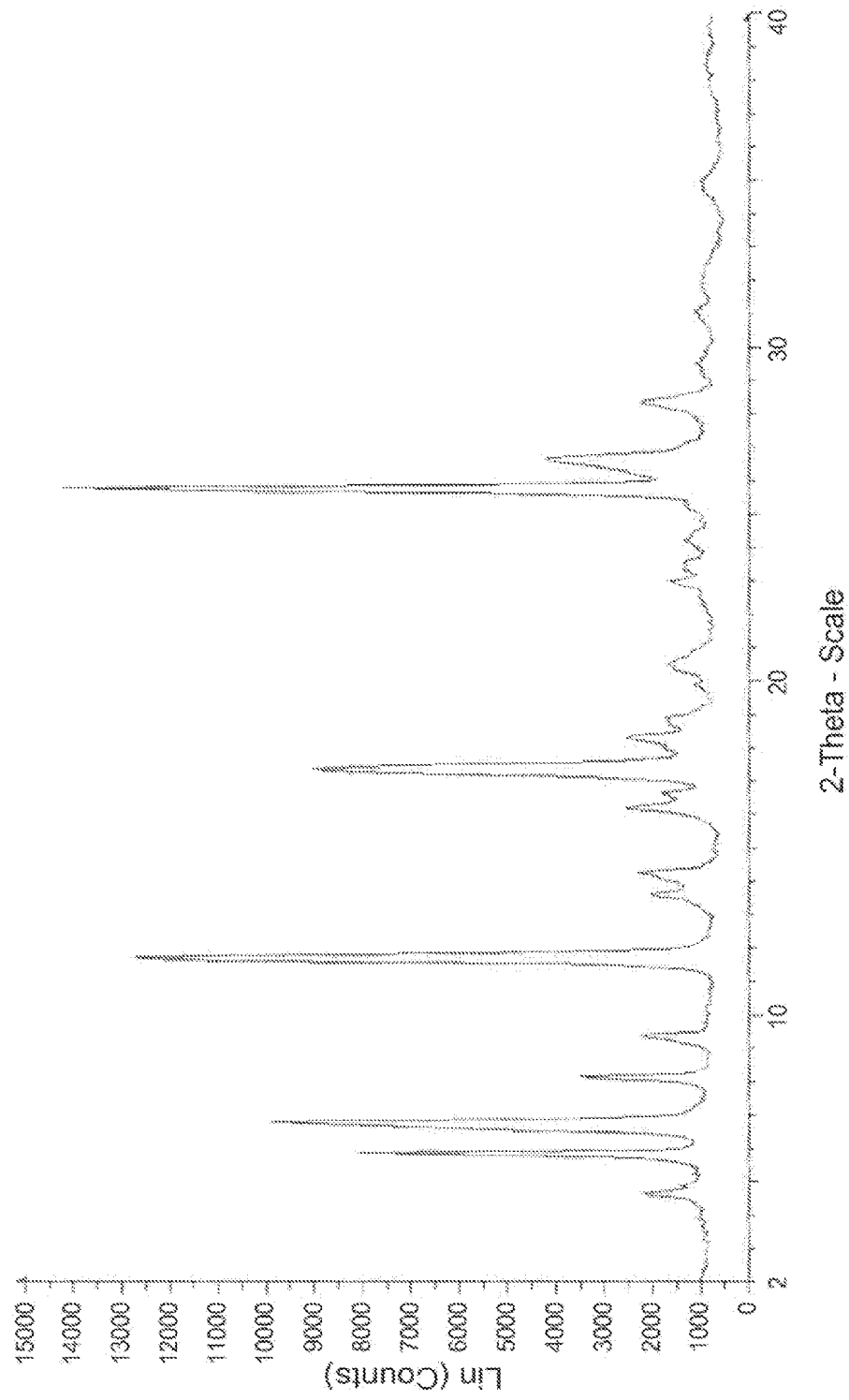
FIG. 1 shows an X-ray powder diffractogram of Febuxostat Form F1.

The present application relates to new polymorphic forms F1-F14 of Febuxostat. In some embodiments, the polymorphs of Febuxostat of the invention are substantially free of any other polymorphic forms, or of specified polymorphic forms In particular, forms F1, F2 and F10 are substantially free of any other polymorph forms or of specified polymorph forms. In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of any other polymorph or of a specified polymorph. In other embodiments, the polymorphs of Febuxostat of the invention contain from 1% to 20% (w/w), from 5% to 20% (w/w), or from 5% to 10% (w/w) of any other polymorph or of a specified polymorph.

A crystal form may be referred to herein as being characterized by graphical data "as depicted in" a Figure. Such data include, for example, powder X-ray diffractograms and solid state NMR spectra. The skilled person will understand that such graphical representations of data may be subject to small variations, e.g., in peak relative intensifies and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, unless stated otherwise, the XRPD measurements are taken using copper Kα radiation wavelength 1.5418 Å.

A thing, e.g., a reaction mixture, may be characterized herein as being at, or allowed to come to "room temperature, often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval e.g., for the process or step, that spans the time during the night, when that process or step may not be actively observed. This time interval is from about 8 to about 20 hours, or about 10-18 hours, typically about 16 hours.

As used herein, and unless stated otherwise, the term "anhydrous" in relation to crystalline Febuxostat relates to a crystalline Febuxostat which contains not more than 1.5% (w/w), or not more than 1% (w/w) of either water or organic solvents as measured by TGA, for example, Febuxostat which contains between about 0% to about 1% (w/w) of either water or organic solvents as measured by TGA.

Unless indicated otherwise, the solid state forms of the present invention can be dried. Drying may be carried out, for example, at elevated temperature under reduced pressure. The crystalline form can be dried at a temperature from about 40° C. to about 60° C., or about 40° C. and about 50° C. for example, about 40° C. The drying can be carried out under reduced pressure (i.e., less than 1 atmosphere, for example, about 10 mbar to about 100 mbar, or about 10 mbar to about 25 mbar). The drying can take place over a period of about 8 hours to about 36 hours, or about 10 hours to about 24 hours, for example, about 16 hours. Drying can be carried out overnight.

The starting material, Febuxostat, in the processes of the present invention, may be prepared according to the process described in PCT publication no. WO 1992/09279, which is incorporated herein by reference.

WO 1990/0058B5 describes crystalline forms of Febuxostat including crystalline form G. Form G of febuxostat shows an X-ray powder diffraction pattern having characteristic peaks at a reflection angle 2θ of about 6.86, 8.36, 9.60, 11.76, 13.74, 14.60, 15.94, 16.74, 17.56, 20.00, 21.26, 23.72, 24.78, 25.14, 25.74, 26.06, 26.64, 27.92, 28.60, 29.66 and 29.98°.

The present invention addresses a need in the art by providing new crystalline forms F1-F14 of Febuxostat that have at least one or more favorable properties compared with known forms of Febuxostat. In particular, the solid state forms of the present invention can have improved characteristics such as: higher crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

Figure 2:
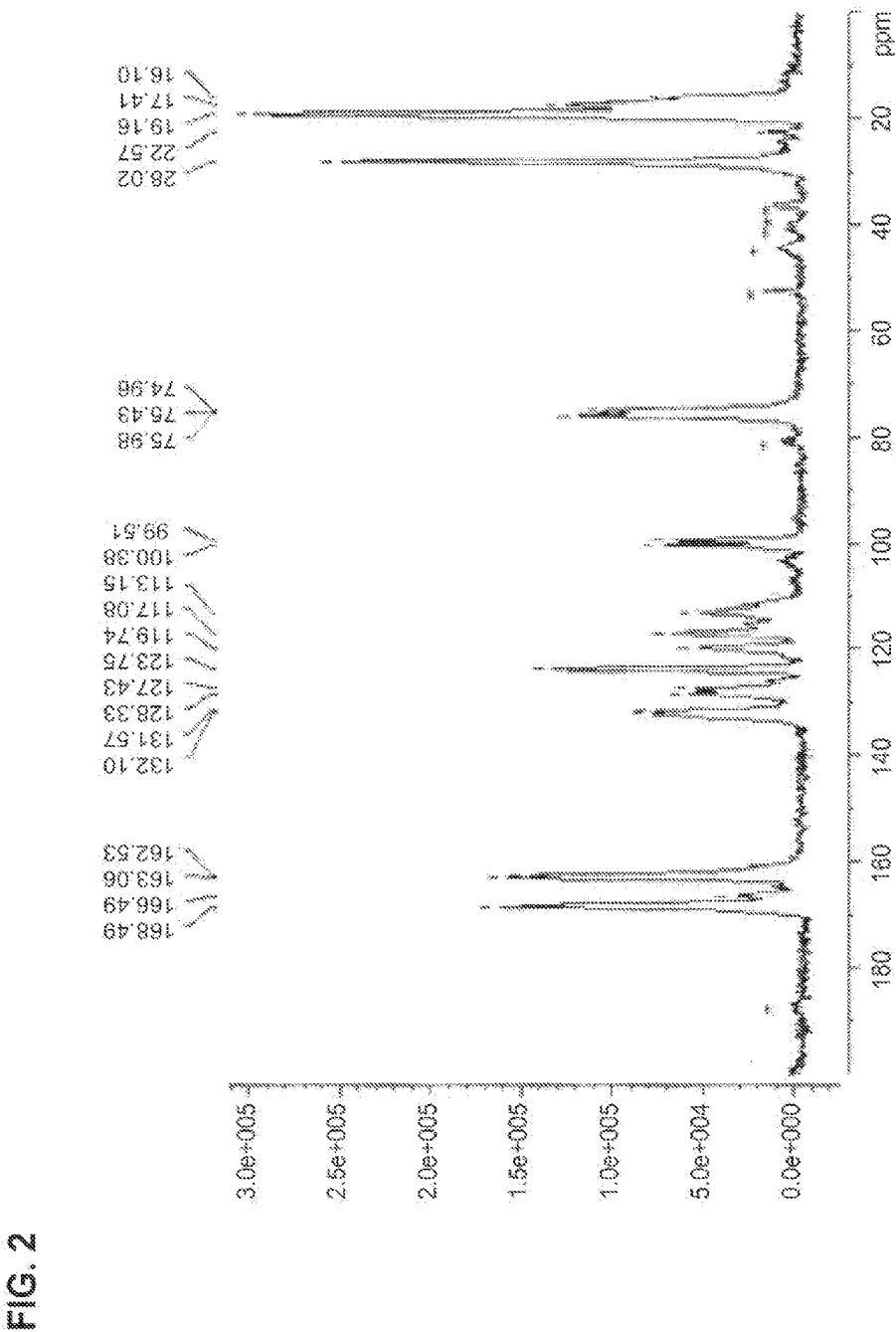
FIG. 2 shows a solid-state $^{13}$C NMR spectrum of Febuxostat Form F1 in the 0-200 ppm range.
Figure 3:
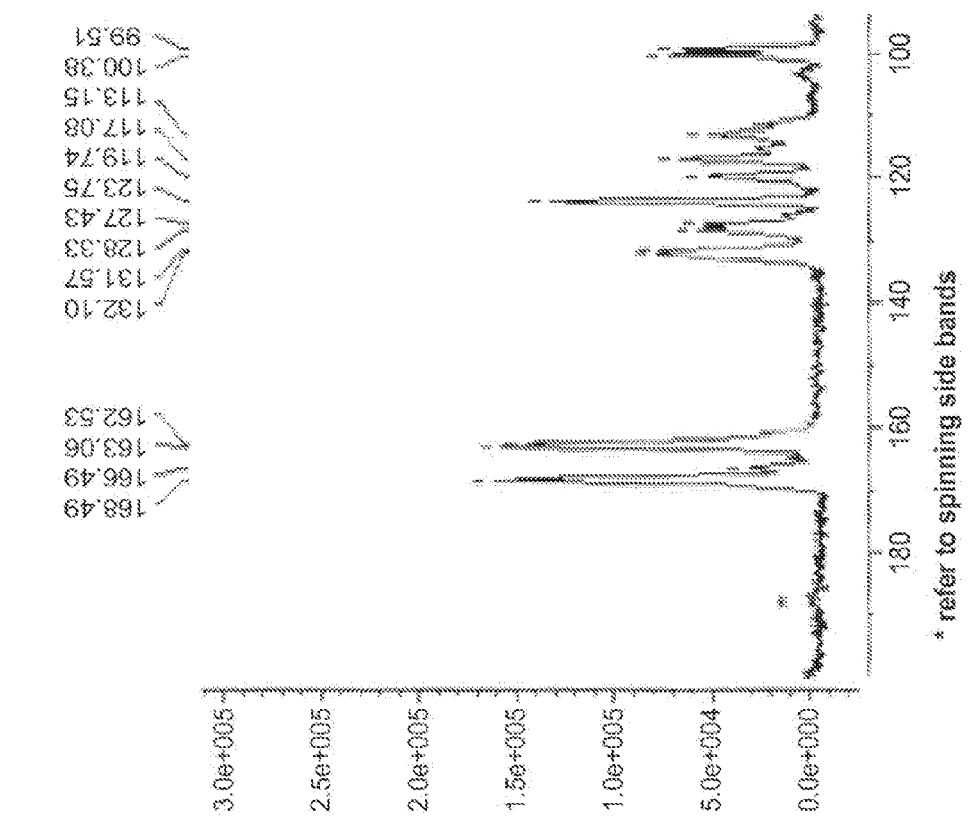
FIG. 3 shows a solid-state $^{13}$C NMR spectrum of Febuxostat Form F1 in the 100-200 ppm range.

The present invention provides crystalline Febuxostat, designated as Form F1. Form F1 can be characterized by data selected from: a powder XRD pattern with peaks at 5.8°; 6.8°, 8.1°, 11.7° and 17.4°±0.2° 2θ; a powder XRD pattern with peaks at 5.8°, 6.8°, 8.1°, 11.8° and 17.4°±0.2° 2θ; an XRPD pattern substantially as depicted in FIG. 1; a solid-state $^{13}$C NMR spectrum with signals at 123.8, 163.1 and 168.5±0.2 ppm; a solid-state $^{13}$C NMR spectrum having chemical shifts differences between the signal exhibiting the lowest chemical shift and another in the chemical shift range of 100 to 180 ppm of 23.4, 62.7 and 68.1±0.1 ppm; a solid-state $^{13}$C NMR spectrum substantially as depicted in FIG. 2 or 3; and combinations thereof. The signal exhibiting the lowest chemical shift in the chemical shift area of 100 to 180 ppm is typically at 100.4±1 ppm. The Febuxostat form F1 as defined in any of the above data, may be further characterized by XRPD pattern having additional peaks at: 4.7°, 9.4°, 14.2°, 16.2°, and 25.8°±0.2° 2θ. Alternatively, the Febuxostat form F1 as defined in any of the above data, may be further characterized by XRPD pattern having additional peaks at: 4.6°, 9.3°, 142°, 16.2°, and 25.8°±0.2° 2θ.

Typically, the febuxostat form F1 is substantially free of Form G, particularly, a powder XRD pattern of form F1 does not have any of the peaks at 21.3° 24.8° and 25.1°±0.2° 2θ.

Febuxostat form F1 has advantageous properties selected from at least one of: chemical purity, flowability, solubility/morphology or crystal habit, stability—such as storage stability, stability to dehydration, stability to polymorphic conversion, low hygroscopicity, low content of residual solvents.

Febuxostat Form F1 may be prepared by crystallizing Febuxostat from methylisobutylketone ("MIBK"). The process may comprise dissolving Febuxostat in MIBK to obtain a mixture; precipitating the Febuxostat; and isolating the obtained precipitate. The precipitating may comprise heating; cooling; and optionally maintaining the mixture. The heating may be done to about reflux temperature and the cooling may be done to a temperature of about 40° C. to about 0° C., or to about room temperature. The maintaining is typically done at a temperature of about room temperature, for a time of about 1 to about 24 hours, or for about 1 to about 12 hours, for example, for about 1.5 hours. The isolation of the precipitate may be done by filtering and washing with a solvent such as MIBK. Optionally, the isolated precipitate is further dried.

Figure 4:
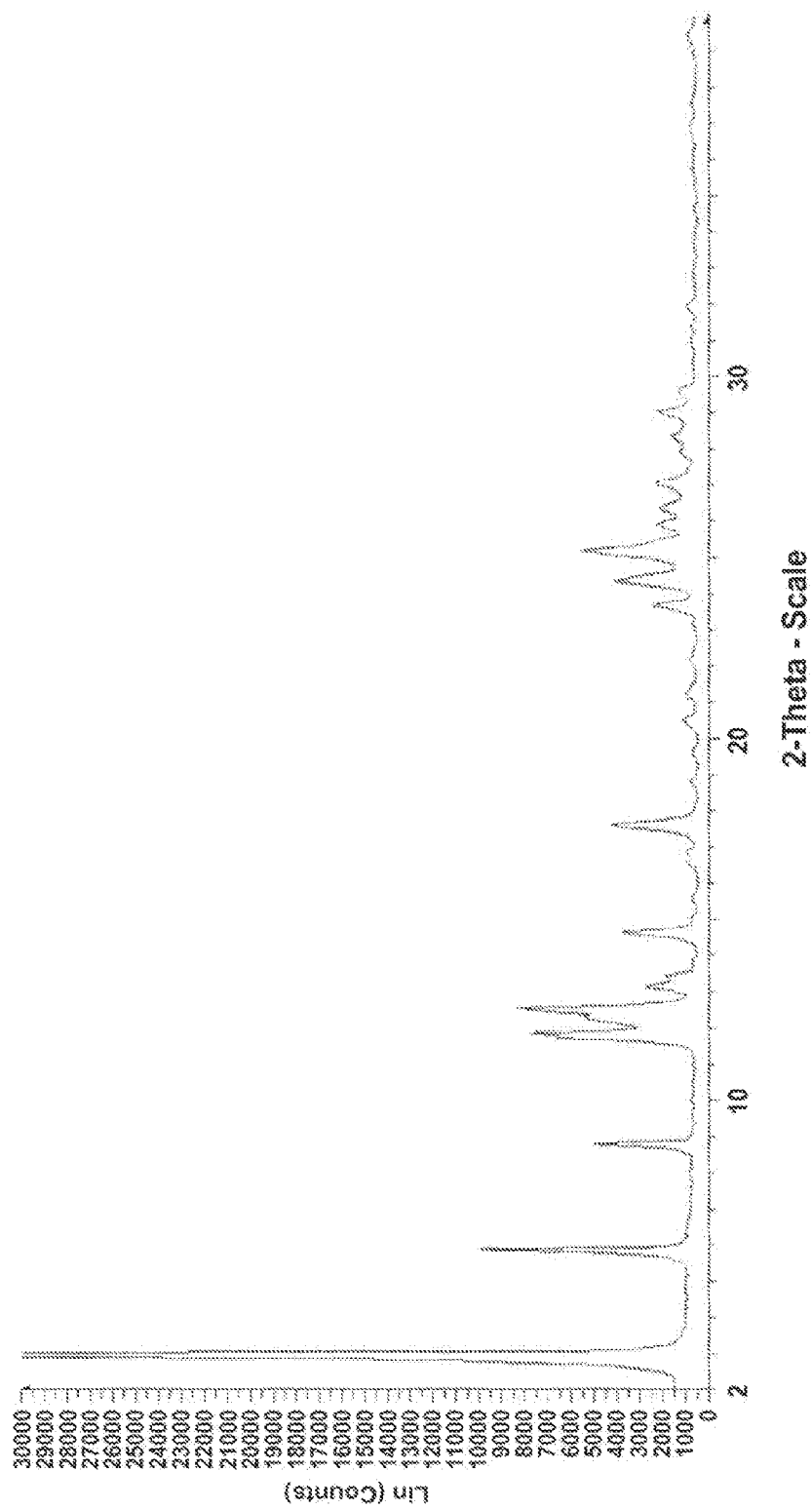
FIG. 4 shows an X-ray powder diffractogram of Febuxostat Form F2.
Figure 5:
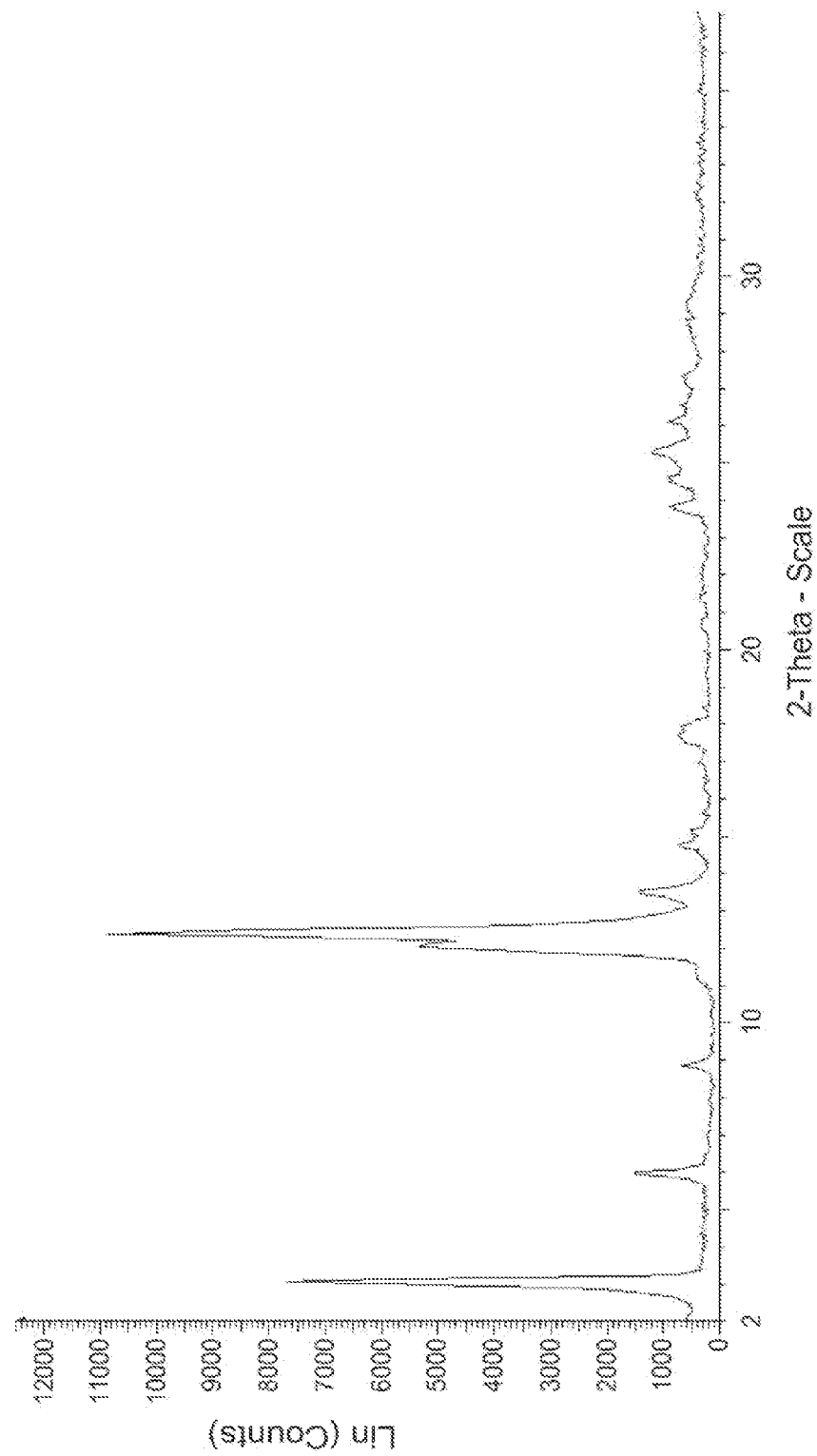
FIG. 5 shows an X-ray powder diffractogram of Febuxostat Form F2.
Figure 6:
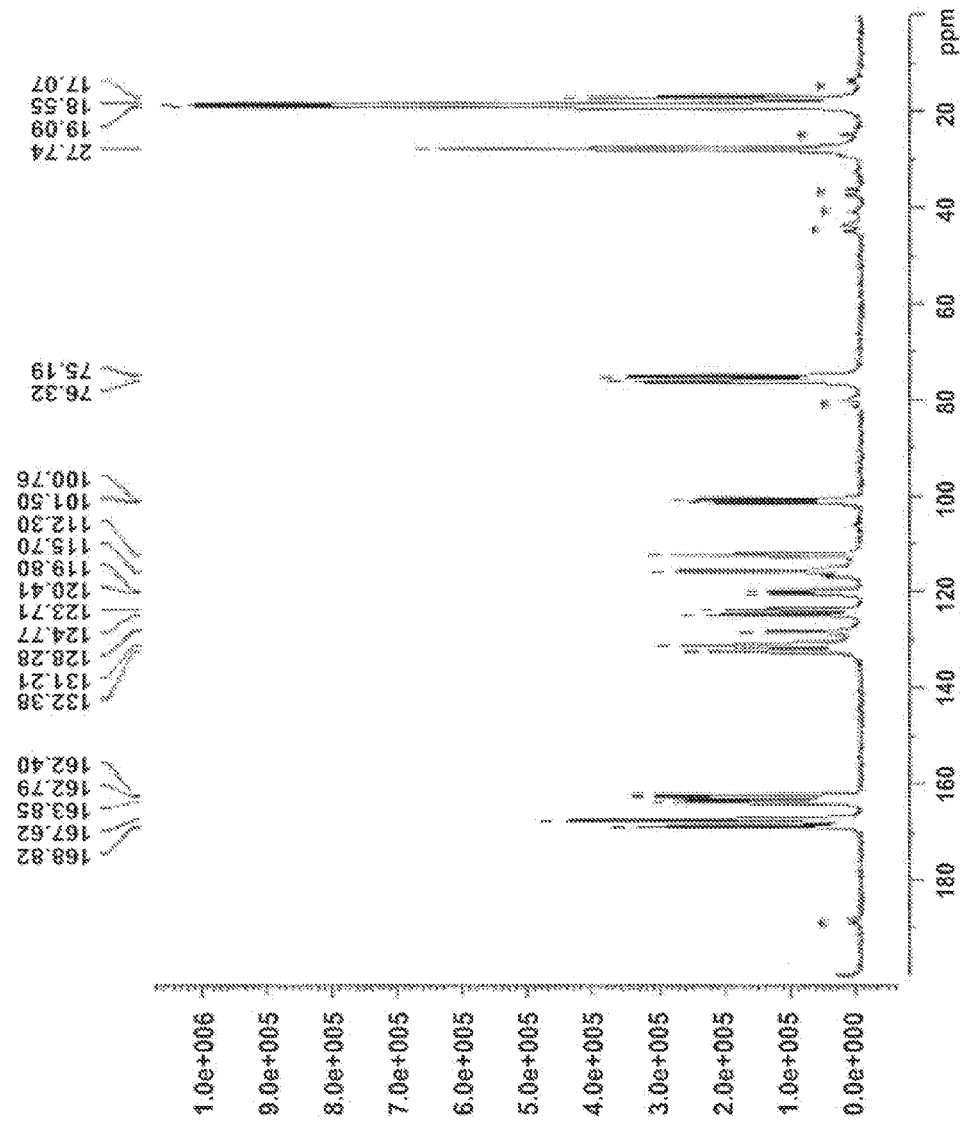
FIG. 6 shows a solid-state $^{13}$C NMR spectrum of Febuxostat Form F2 in the 0-200 ppm range.
Figure 7:
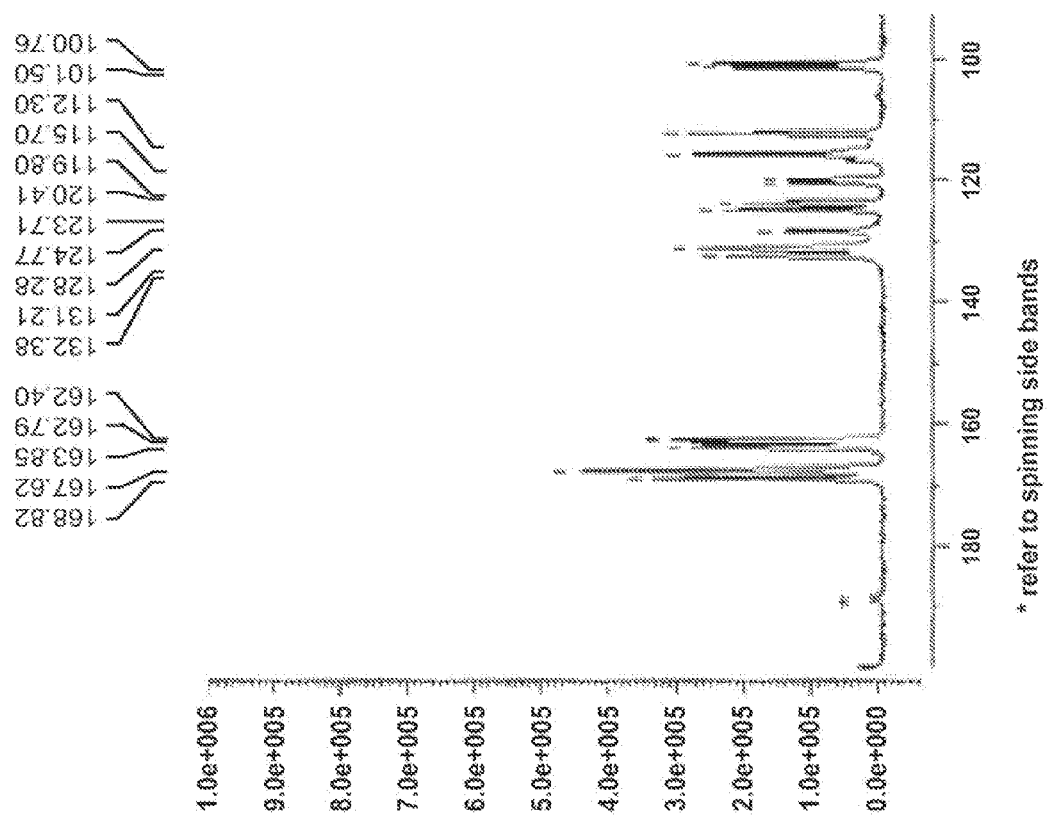
FIG. 7 shows a solid-state $^{13}$C NMR spectrum of Febuxostat Form F2 in the 100-200 ppm range.

The present invention provides a crystalline Febuxostat, designated as Form F2. Form F2 can be characterized by data selected from: a powder XRD pattern with peaks at 2.9°, 5.9°, 8.7°, 11.8° and 12.5°±0.2° 2θ; a powder XRD pattern with peaks at 3.0°, 5.9°, 8.8°, 11.8° and 12.5°±0.2° 2θ; and XRPD pattern substantially as depicted in FIG. 4 or FIG. 5; a solid-state $^{13}$C NMR spectrum with signals 112.3, 163.9, 168.8±0.2 ppm; a solid-state $^{13}$C NMR spectrum having chemical shifts differences between the signal exhibiting the lowest chemical shift and another in the chemical shift range of 100 to 180 ppm of 11.5, 63.1 and 68.0±0.1 ppm; a solid-state $^{13}$C NMR spectrum substantially as depicted in FIG. 6 or 7; and combinations thereof. The signal exhibiting the lowest chemical shift in the chemical shift area of 100 to 180 ppm is typically at 100.8±0.1 ppm. The Febuxostat form F2 as defined in any of the above data, may be further characterized by additional XRPD peaks at: 13.1°, 14.7°, 17.5°, 24.4° and 25.2° 2θ. Alternatively, the Febuxostat form F2 as defined in any of the above data, may be further characterized by additional XRPD peaks at 13.1°, 14.6°, 17.6°, 24.4° and 25.5°±0.2° 2θ.

Febuxostat form F2 may be anhydrous.

Febuxostat form F2 has advantageous properties selected from at least of: chemical purity, flowability, solubility, morphology or crystal habit, stability—such as storage stability, stability to dehydration, stability to polymorphic conversion, low hygroscopicity, low content of residual solvents. In particular, the crystalline Febuxostat form F2 of the present invention has advantageous morphology compared with other crystalline forms such as forms A, B and C of Febuxostat. While forms A, B and C of Febuxostat are all needle shaped, Febuxostat form F2 has plate morphology, and therefore has better technological properties, such as compactability, which may be better for e.g. tablet formulation.

Febuxostat Form F2 may be prepared by crystallizing Febuxostat from a mixture comprising a solvent selected from: methylethylketone ("MEK") and acetone, in combination with a $C_5$-$C_8$ hydrocarbon.

The crystallization, which may be done at about room temperature, typically comprises dissolving Febuxostat in a solvent selected from: MEK and acetone; and adding a $C_5$-$C_8$ hydrocarbon, such as n-heptane or n-hexane, to obtain a mixture comprising Febuxostat crystalline form F2. The mixture may be maintained at about room temperature for a time of about 1 hour to about 48 hours, or for about 1 hour to about 24 hours. The obtained crystalline form may be further recovered, e.g., by filtering and drying.

The above Febuxostat Form F2 may also be prepared by a process comprising slurrying Febuxostat form F3 as defined below in dichloromethane ("DCM"), at about room temperature, to obtain a mixture. The mixture may be maintained for a time of from about 1 hour to about 48 hours, for example, for about 25 hours. The obtained crystalline form may be further isolated, e.g., by filtration. The isolated crystalline form is further dried.

Figure 8:
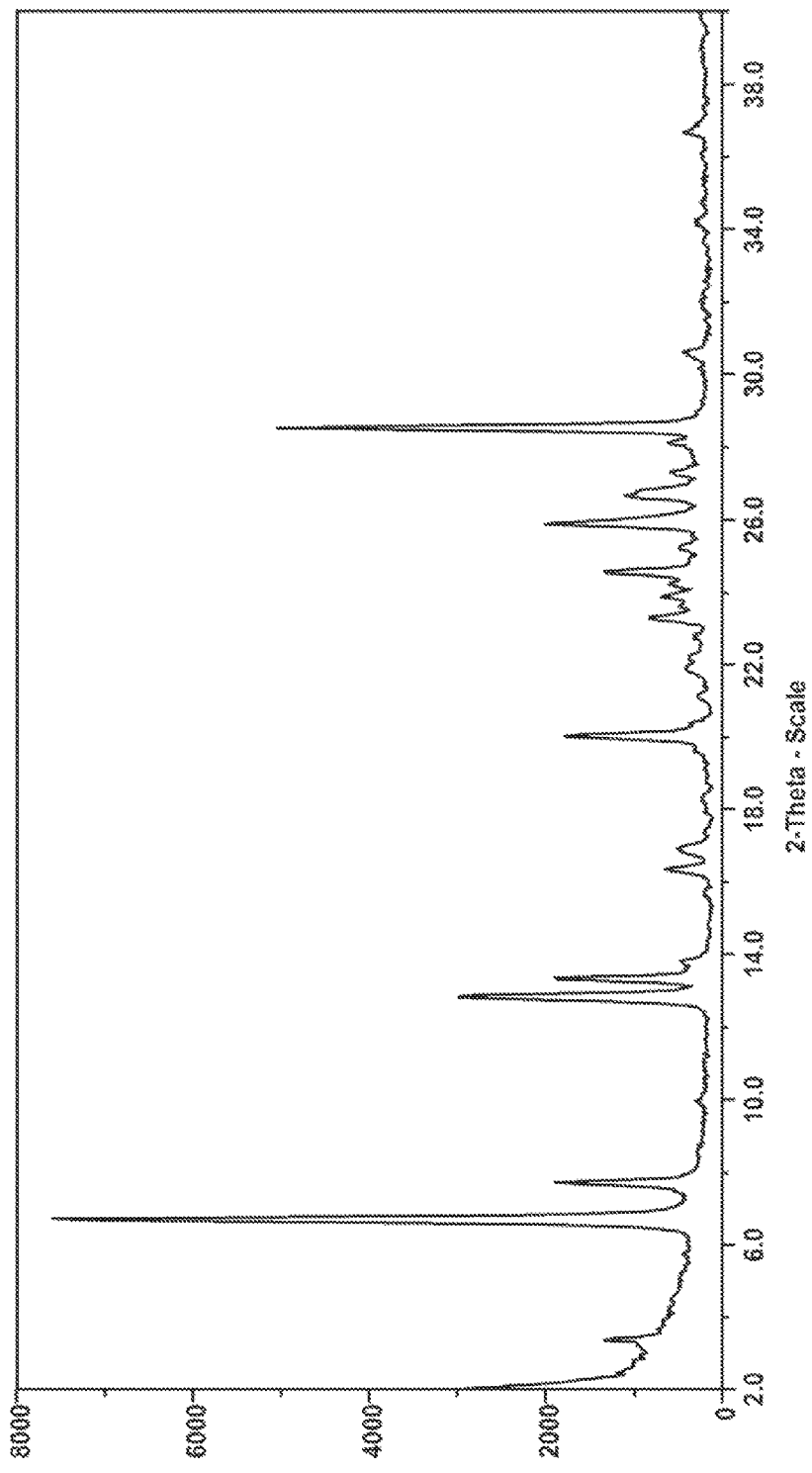
FIG. 8 shows an X-ray powder diffractogram of Febuxostat Form F10.
Figure 9:
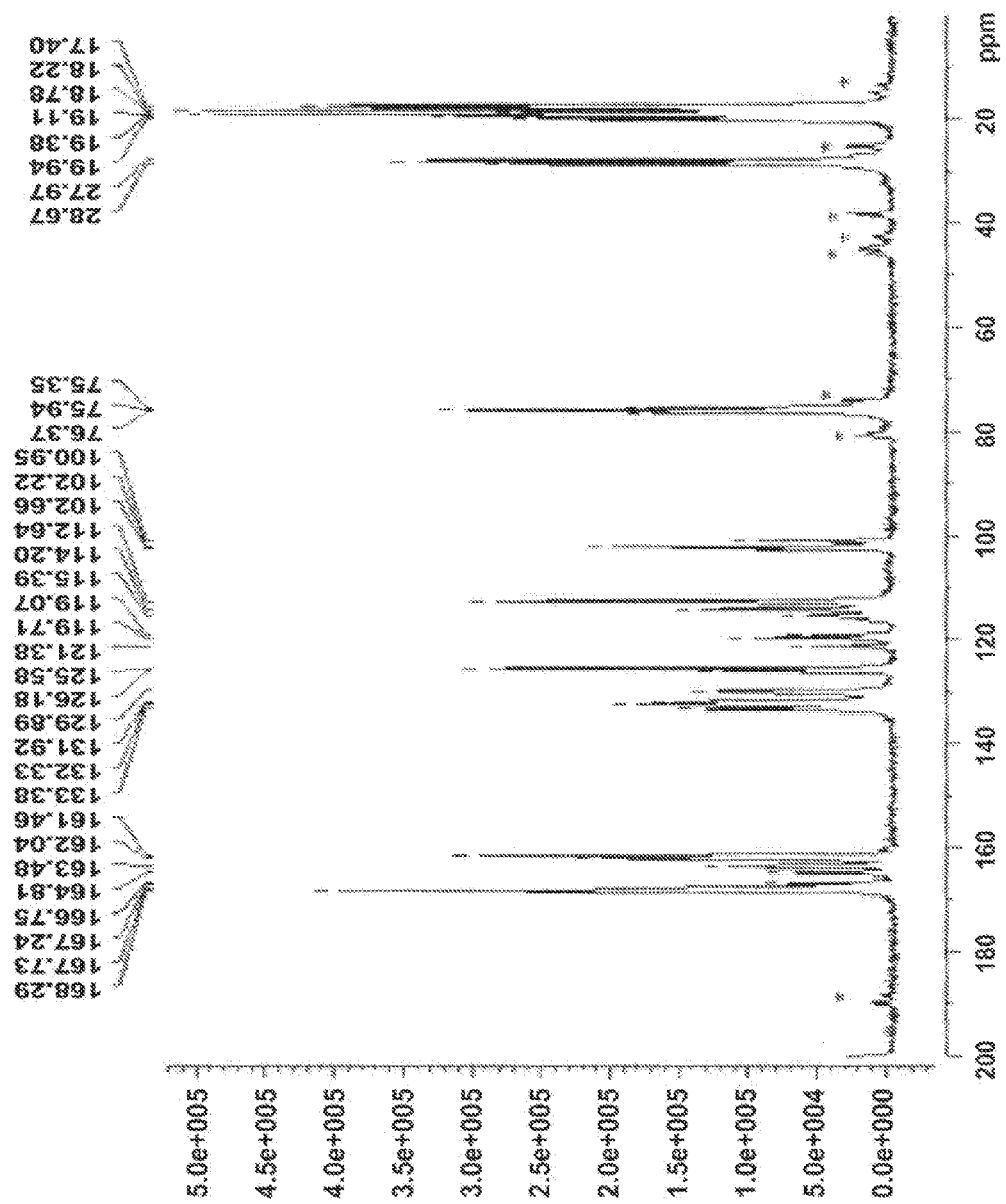
FIG. 9 shows a solid-state $^{13}$C NMR spectrum of Febuxostat Form F10 in the 0-200 ppm range.
Figure 10:
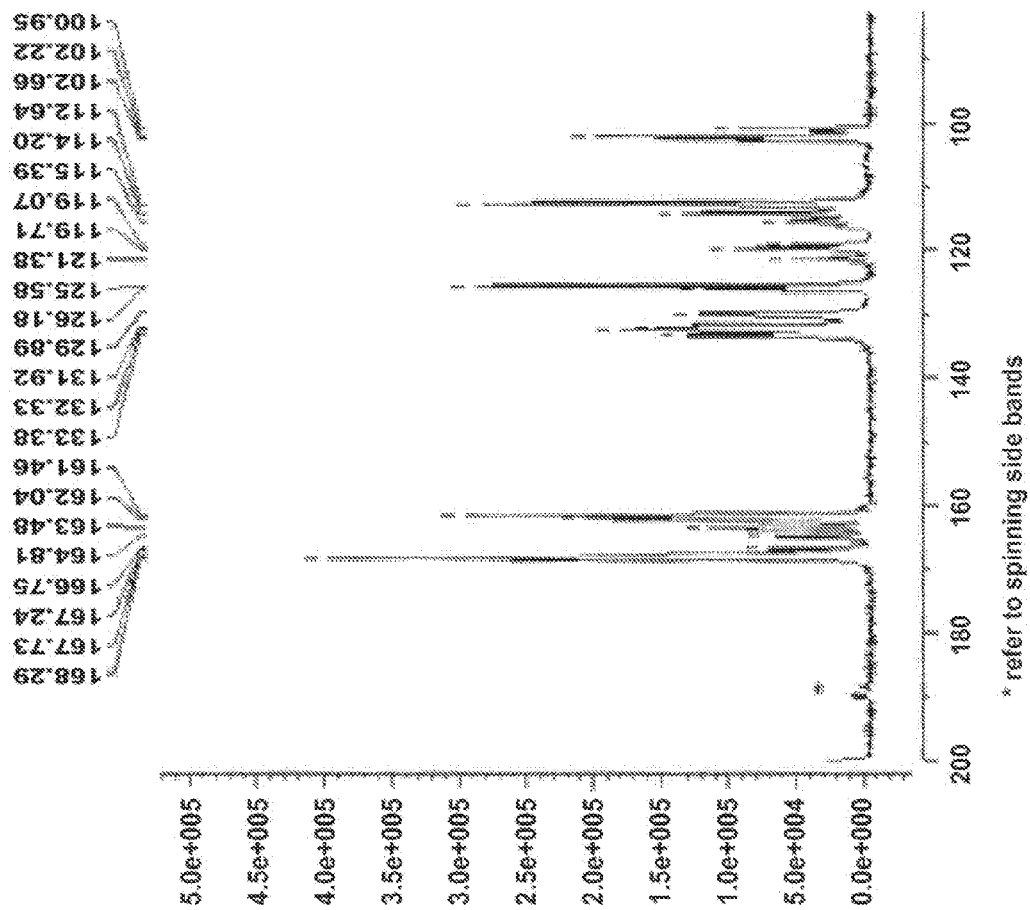
FIG. 10 shows a solid-state $^{13}$C NMR spectrum of Febuxostat Form F10 in the 100-200 ppm range.

The present invention encompasses crystalline Febuxostat, designated as form F10. Form F10 can be characterized by data selected from: an X-ray powder diffraction pattern having peaks at: 6.7°, 7.7°, 12.8°, 13.3° and 20.0°±0.2° 2θ; an X-ray powder diffraction pattern substantially as depicted in FIG. 8; a solid-state $^{13}$C NMR spectrum with signals at 112.7, 125.7, 132.4, and 168.3±0.2 ppm; a solid-state $^{13}$C NMR spectrum having chemical shifts differences between the signal exhibiting the lowest chemical shift and another in the chemical shift range of 100 to 180 ppm of 11.7, 24.7, 31.4 and 67.3±0.1 ppm; a solid-state $^{13}$C NMR spectrum substantially as depicted in FIG. 9 or 10; and combinations thereof. The signal exhibiting the lowest chemical shift in the chemical shift area of 100 to 180 ppm is typically at 101.0±1 ppm. The Febuxostat form F10 as defined in any of the above data, may be further characterized by additional XRPD peaks at 3.3°, 16.3°, 16.9°, 24.5° and 25.8°±0.2° 2θ.

Febuxostat form F10 may be anhydrous.

Febuxostat form F10 has advantageous properties selected from at least one of: chemical purity, flowability, solubility, morphology or crystal habit, stability—such as storage stability, stability to dehydration, stability to polymorphic conversion, low hygroscopicity, low content of residual solvents. In particular, the crystalline Febuxostat form F10 of the present invention has better solubility in ethanol compared to other crystalline forms.

The present invention also encompasses a process for preparing Febuxostat Form F10 comprising crystallizing Febuxostat from a mixture comprising methylisobutylketone ("MIBK") and a $C_5$-$C_8$ hydrocarbon.

The crystallization may comprise dissolving Febuxostat in MIBK; and adding a $C_5$-$C_8$ hydrocarbon such as n-heptane or n-hexane, to obtain a mixture comprising said crystalline form. The addition of the $C_5$-$C_8$ hydrocarbon may be done dropwise, at about reflux temperature. The dissolution is typically done while heating, e.g., to about reflux temperature.

The process may further comprise cooling to a temperature of about 40° C. to about 0° C., or to about room temperature. The obtained crystalline form may be further isolated, e.g., by filtering and drying.

Figure 11:
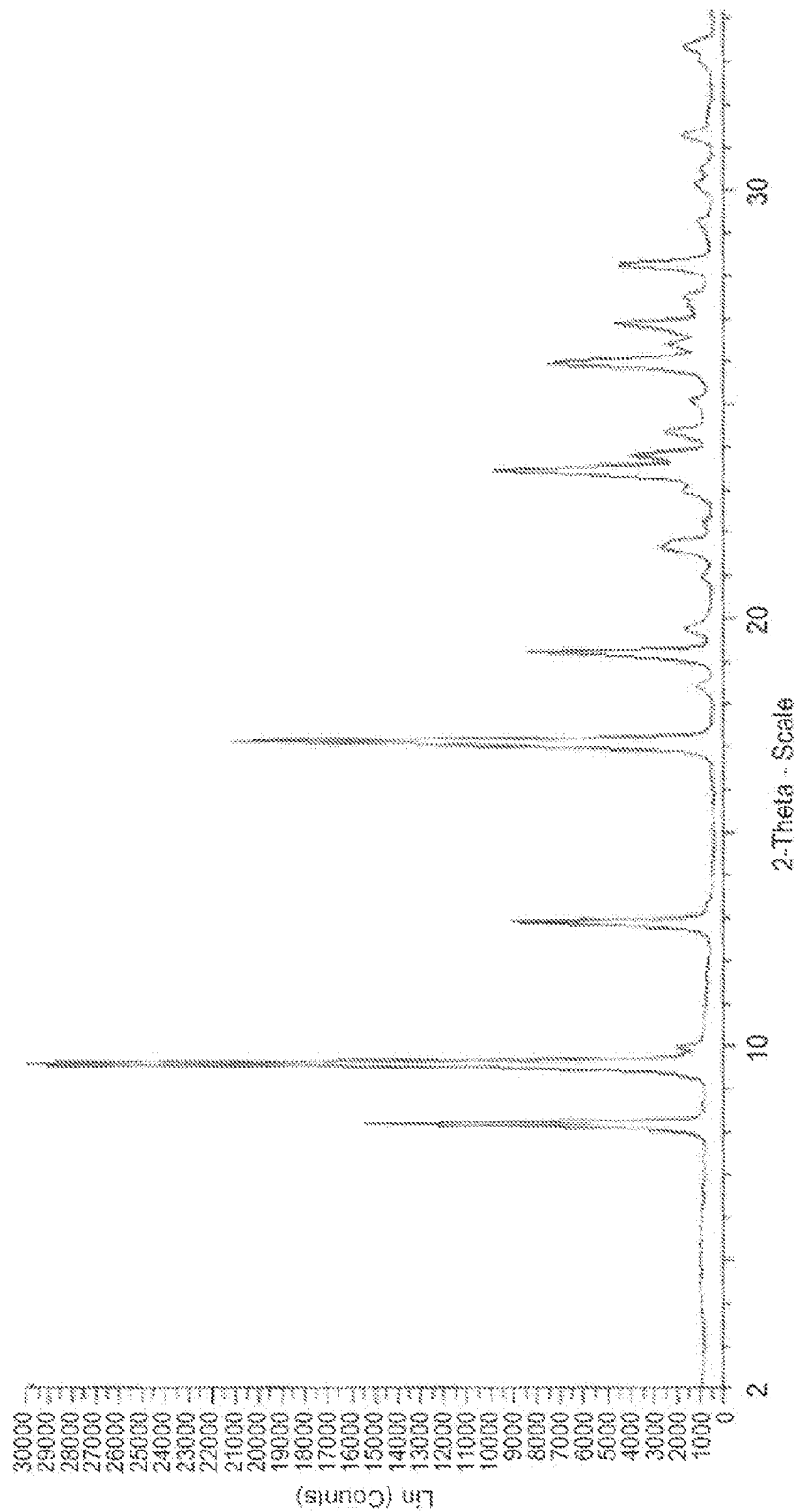
FIG. 11 shows an X-ray powder diffractogram of Febuxostat Form F3.
Figure 12:
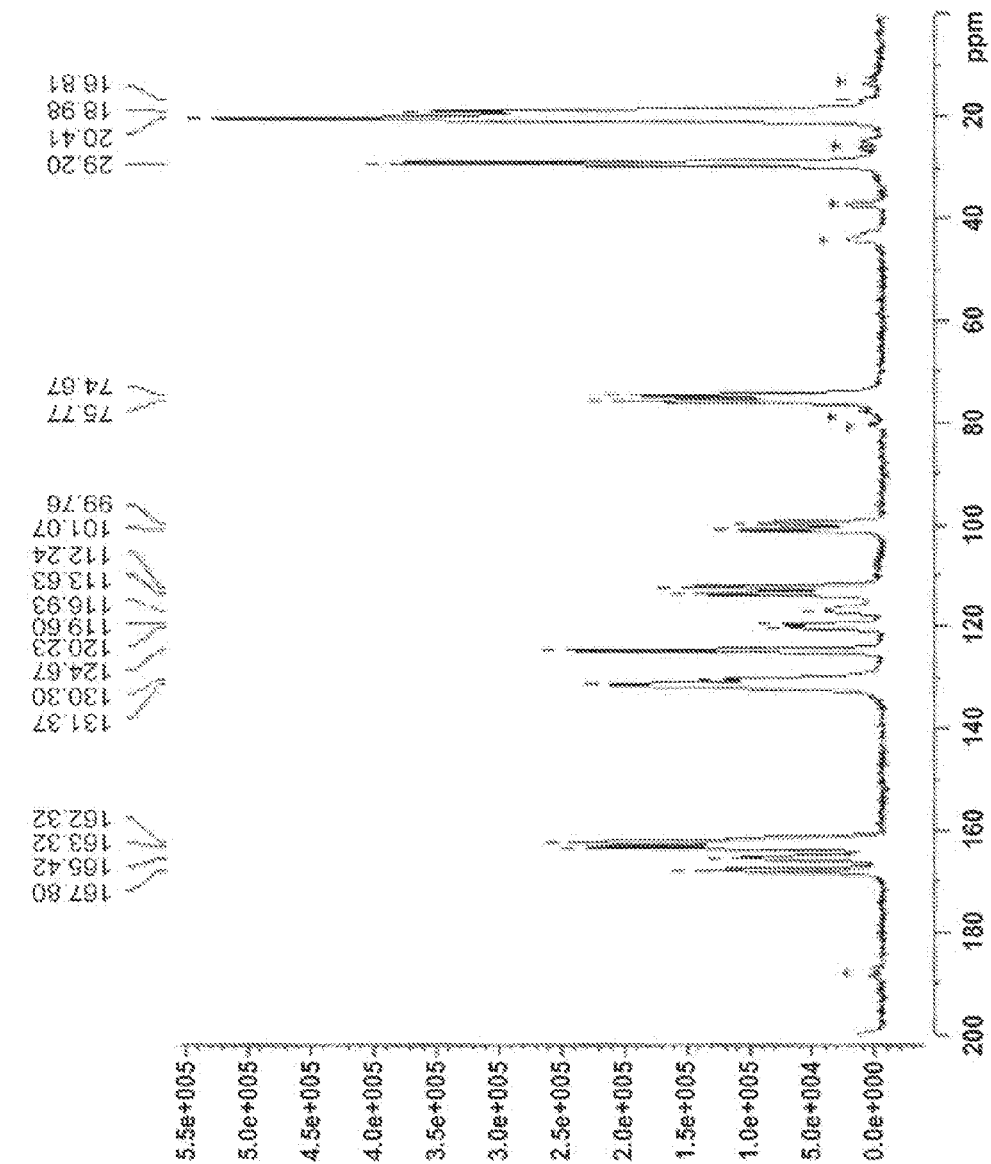
FIG. 12 shows a solid-state $^{13}$C NMR spectrum of Febuxostat Form F3 in the 0-200 ppm range.
Figure 13:
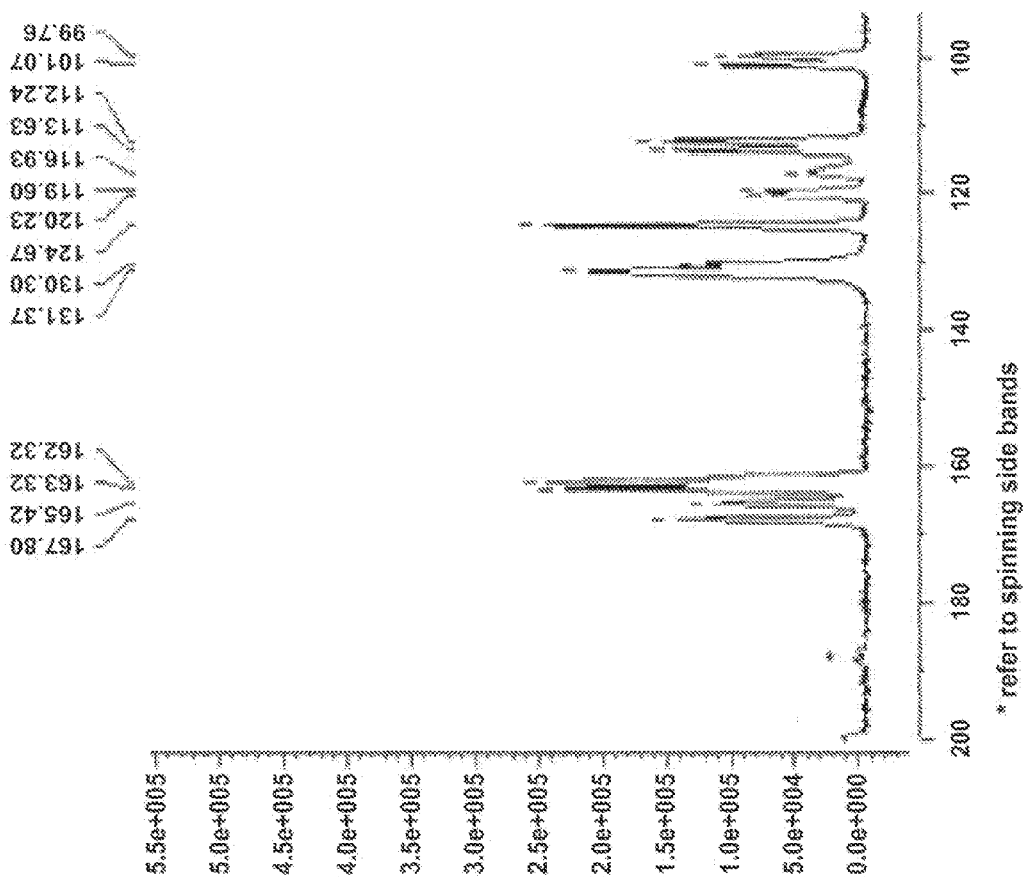
FIG. 13 shows a solid-state $^{13}$C NMR spectrum of Febuxostat Form F3 in the 100-200 ppm range.

The present invention provides a crystalline Febuxostat, designated as Form F3. Form F3 can be characterized by data selected from: a powder XRD pattern with peaks at 8.2°, 9.5°, 12.9°, 17.1° and 19.2°±0.2° 2θ; an XRPD pattern substantially as depicted in FIG. 11; a solid-state $^{13}$C NMR spectrum with signals at 131.4, 162.3 and 165.4±0.2 ppm; a solid-state $^{13}$C NMR spectrum having chemical shifts differences between the signal exhibiting the lowest chemical shift and another in the chemical shift range of 100 to 180 ppm of 30.3, 61.2 and 64.3±0.1 ppm; a solid-state $^{13}$C NMR spectrum substantially as depicted in FIG. 12 or 13; and combinations thereof. The signal exhibiting the lowest chemical shift in the chemical shift area of 100 to 180 ppm is typically at 101.1±1 ppm. The Febuxostat Form F3 as defined in any of the above data may be further characterized by additional XRPD peaks at: 21.6°, 23.5°, 24.3°, 26.0° and 26.9°±0.2° 2θ.

The present invention encompasses a process for preparing Febuxostat Form F3 comprising crystallizing Febuxostat from EtOH. The crystallization may comprise: dissolving Febuxostat in EtOH; heating to a temperature such as reflux temperature; cooling to a temperature such as, about 30° C. to about 0° C., or to a temperature of about 15° C. to about 5° C., for example, to a temperature of about 5° C. The process may further comprise a maintaining step at a temperature such as, about 0° C. to about 30° C., or at a temperature of about 5° C. to about 15° C., for example, at a temperature of about 5° C., for a time interval such as, about 1 hour to about 48 hours, or about 1 hour to about 24 hours, for example, about 1.5 hours, to obtain crystalline form F3 of Febuxostat. The obtained crystalline form may be further recovered, e.g., by filtering and drying.

Figure 14:
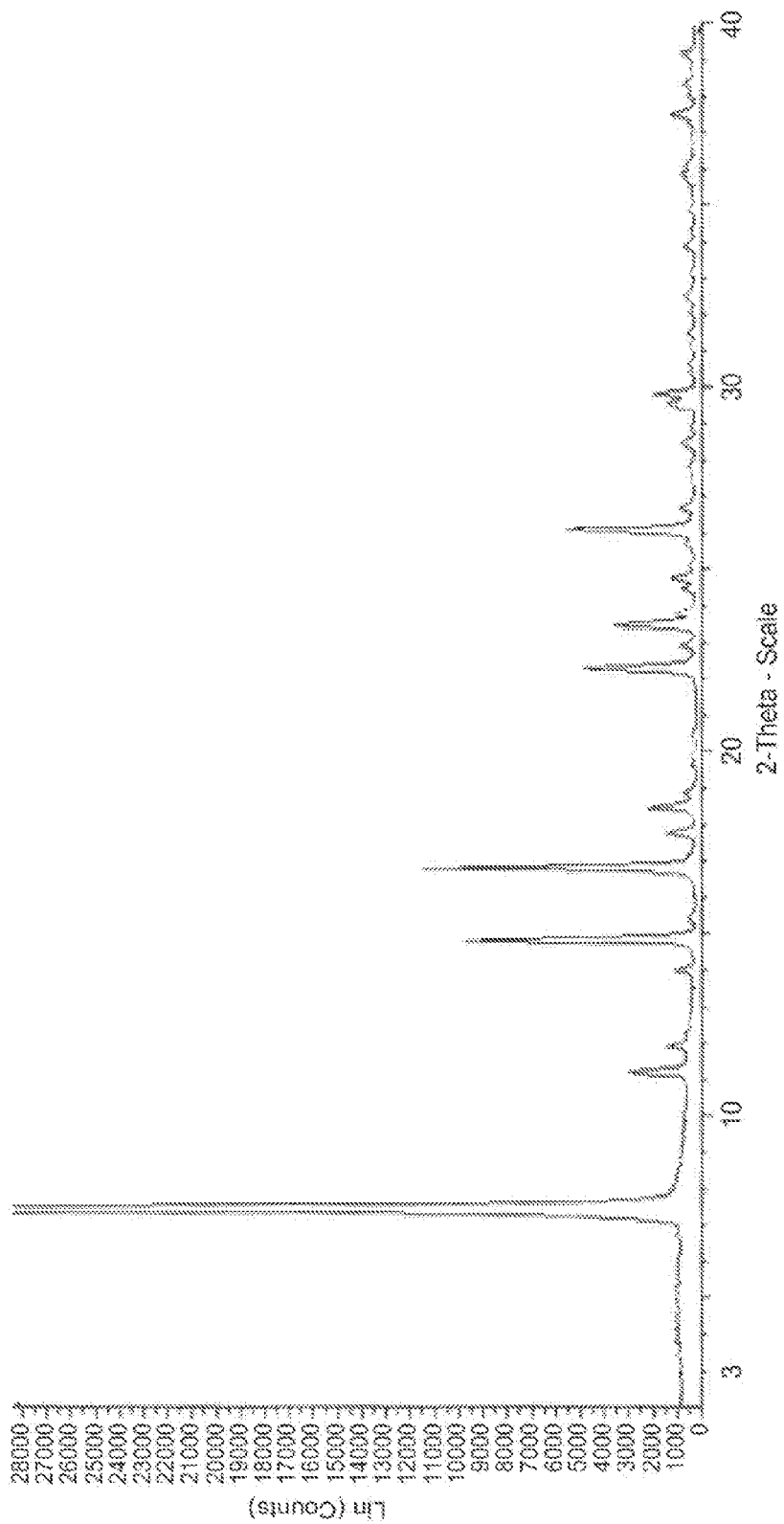
FIG. 14 shows an X-ray powder diffractogram of Febuxostat Form F4.
Figure 15:
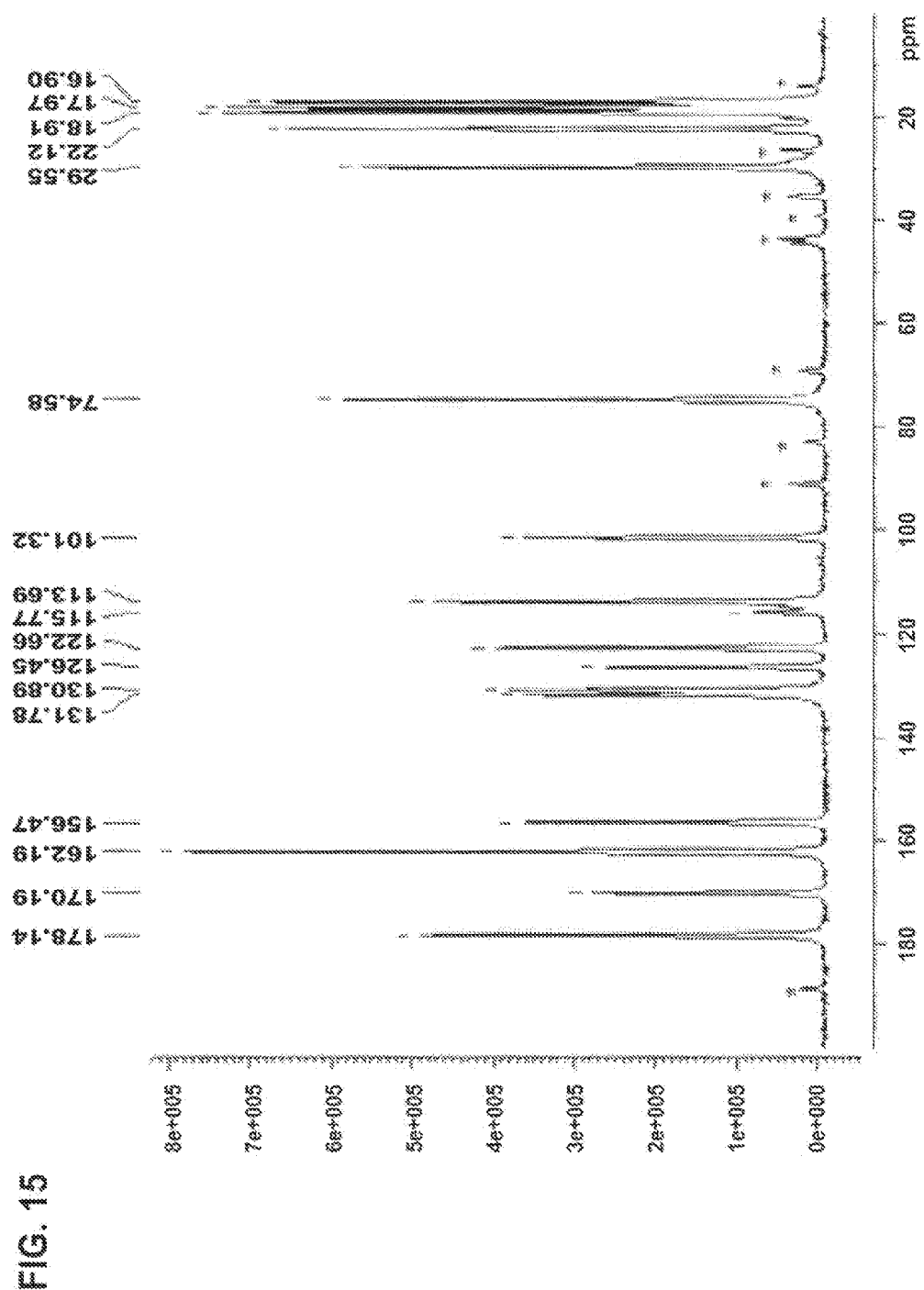
FIG. 15 shows a solid-state $^{13}$C NMR spectrum of Febuxostat Form F4 in the 0-200 ppm range.
Figure 16:
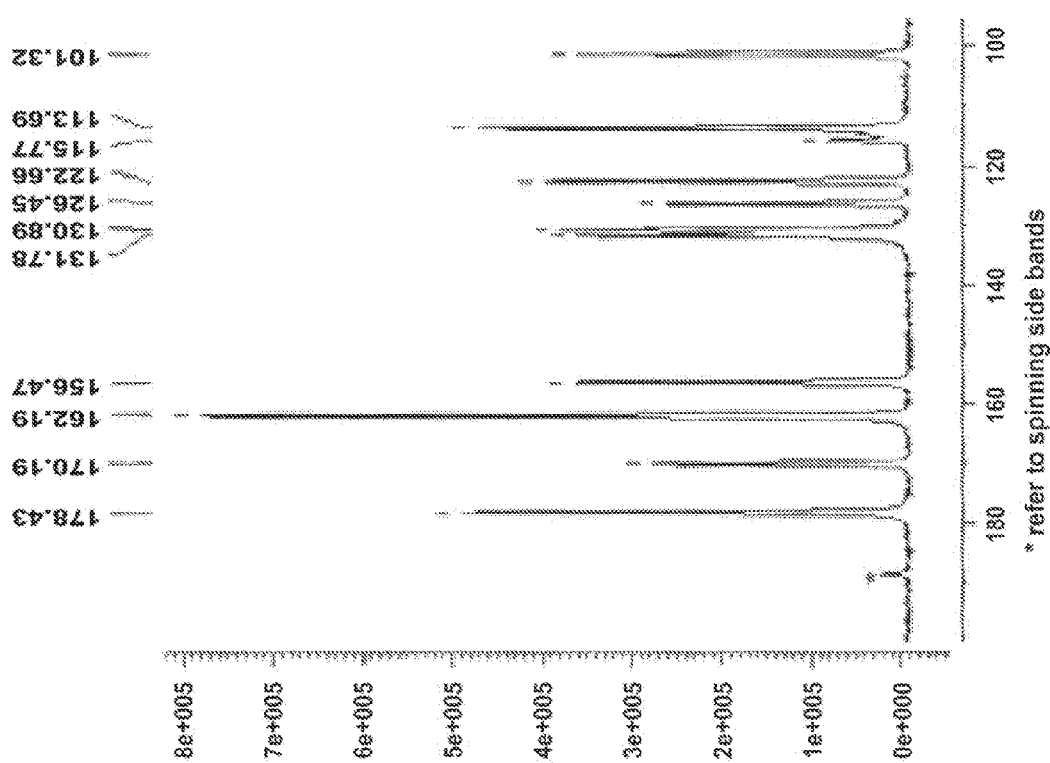
FIG. 16 shows a solid-state $^{13}$C NMR spectrum of Febuxostat Form F4 in the 100-200 ppm range.

The present invention encompasses crystalline Febuxostat, designated as Form F4. Form F4 can be characterized by data selected from: an X-ray powder diffraction pattern having peaks at 7.4°, 11.2°, 14.8°, 16.8° and 22.3°±0.2° 2θ; an X-ray powder diffraction pattern substantially as depicted in FIG. 14; a solid-state $^{13}$C NMR spectrum with signals at 156.5, 170.2 and 178.4±0.2 ppm; a solid-state $^{13}$C NMR spectrum having chemical shifts differences between the signal exhibiting the lowest chemical shift and another in the chemical shift range of 100 to 180 ppm of 55.2, 68.9 and 77.1±0.1 ppm; a solid-state $^{13}$C NMR spectrum substantially as depicted in FIG. 15 or 16; and combinations thereof. The signal exhibiting the lowest chemical shift in the chemical shift area of 100 to 180 ppm is at 101.3±1 ppm. The Febuxostat Form F4 as defined in any of the above data, may be further characterized by additional X-ray powder diffraction pattern peaks at 11.9°, 17.7°, 18.4°, 23.5° and 26.1°±0.2° 2θ.

The above Febuxostat Form F4 may be prepared by a process comprising precipitating Febuxostat from acetic acid ("AcOH"). In one embodiment, the precipitation may comprise slurrying Febuxostat form F3 in AcOH, at a temperature such as about room temperature, to obtain a mixture. The mixture may be maintained at about room temperature for a time interval such as about 1 hour to about 48 hours, or for about 20 hours to about 30 hours, for example, for about 25 hours.

In another embodiment, the precipitation comprises crystallizing Febuxostat from AcOH. The crystallization may comprise dissolving, typically, while heating to a temperature such as reflux temperature; and then cooling to a temperature such as about 0° C. to about 40° C., or to about room temperature to obtain said crystalline form. The process may further comprise a maintaining step wherein the cooled mixture is maintained at a temperature, e.g., about room temperature, for a time of about 1 hour to about 48 hours, or for about 1 hour to about 24 hours, for example, for about 3.5 hours. The obtained crystalline form may be further isolated, e.g., by filtration.

Figure 17:
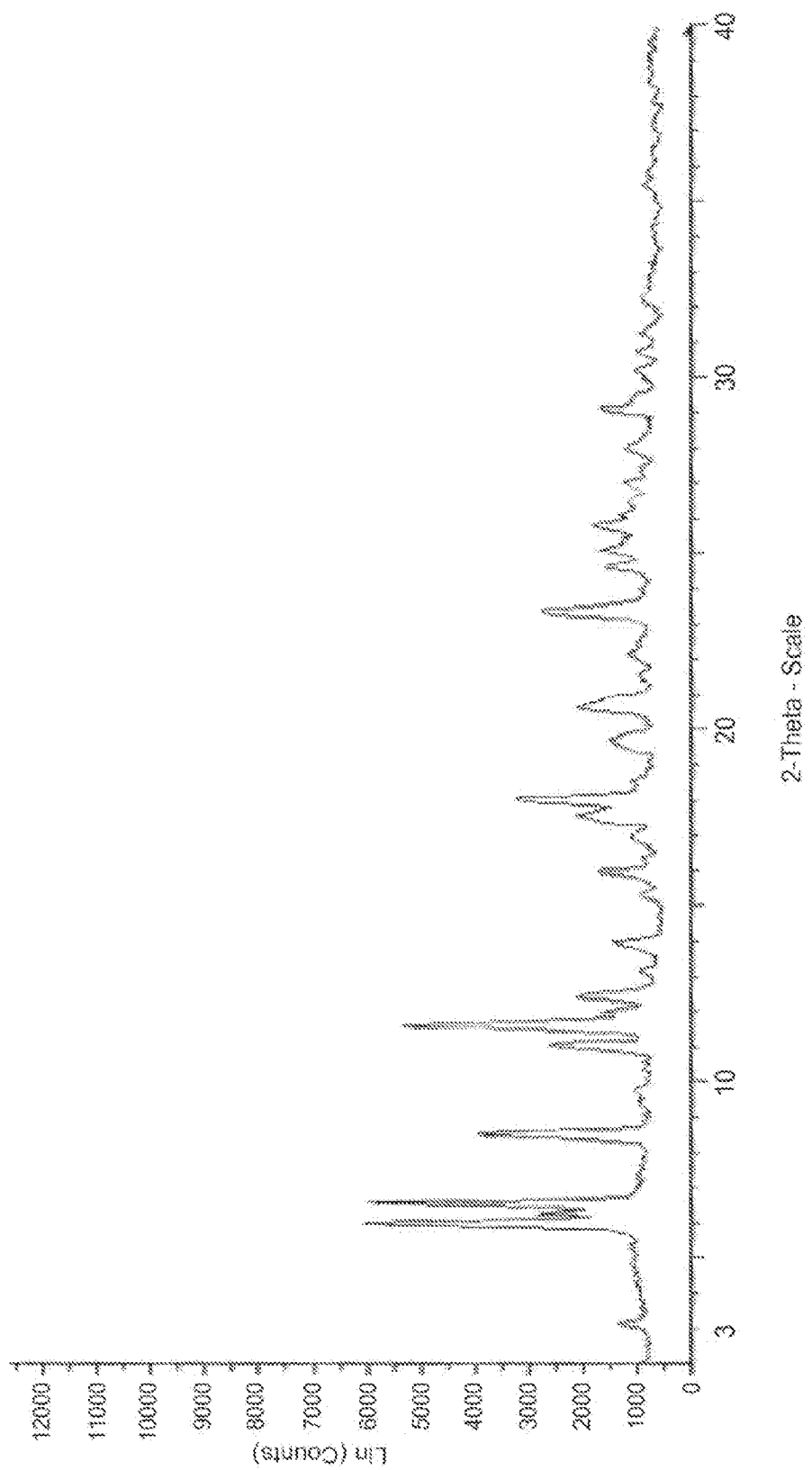
FIG. 17 shows an X-ray powder diffractogram of Febuxostat Form F5.

The present invention encompasses crystalline Febuxostat designated as Form F5. Form F5 can be characterized by data selected from: an X-ray powder diffraction pattern having peaks at 5.9°, 6.5°, 8.5°, 11.6° and 18.0°±0.2° 2θ; an X-ray powder diffraction pattern substantially as depicted in FIG. 17; and combinations thereof. The Febuxostat Form F5 as defined in any of the above data, may be further characterized by additional XRPD peaks at 11.0°, 12.4°, 17.5°, 20.7° and 23.3°±0.2° 2θ.

The present invention also encompasses a process for preparing Febuxostat Form F5 comprising crystallizing febuxostat from a mixture comprising dimethylacetamide ("DMA") and n-heptane. The crystallization may comprise dissolving Febuxostat in DMA; and adding n-heptane to obtain said crystalline form. The process may be done at about room temperature. The process may further comprise a maintaining step, wherein the mixture is maintained, e.g. at about room temperature, for about 1 hour to about 72 hours, or for about 1 hour to about 48 hours, for example, for about 43 hours.

Figure 18:
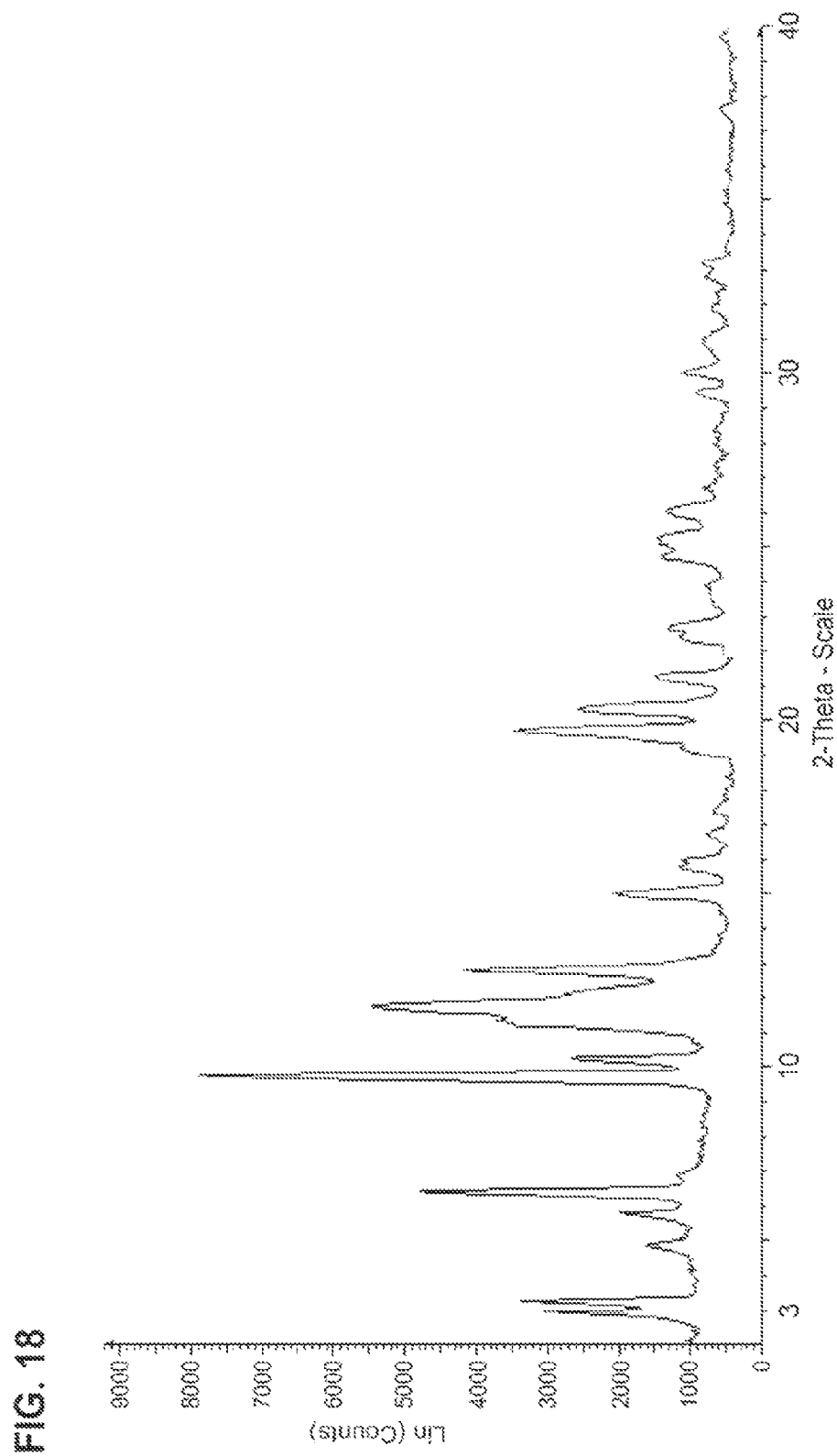
FIG. 18 shows an X-ray powder diffractogram of Febuxostat Form F6.

The present invention encompasses crystalline febuxostat, designed as Form F6. Form F6 can be characterized by data selected from: an X-ray powder diffraction pattern having peaks at 2.9°, 6.4°, 9.7°, 11.7° and 12.8°±0.2° 2θ; and X-ray powder diffraction pattern substantially as depicted in FIG. 18; and a combination thereof. The febuxostat Form F6 as defined in any of the above data, may be further characterized by additional XRPD peaks at 3.2°, 10.2°, 15.0°, 19.7° and 20.3°±0.2° 2θ.

The present invention encompasses a process for preparing Febuxostat Form F6 comprising crystallizing Febuxostat from chloroform. The crystallization may comprise dissolving Febuxostat in chloroform; heating; and then cooling to obtain a suspension comprising said crystalline form. The heating may be done to a temperature such as about reflux temperature, and the cooling may be done to a temperature of about 40° C. to about 0° C., or to about room temperature. The process may further comprise a maintaining step, wherein the cooled mixture is maintained, e.g., at about room temperature, for a time such as about 1 hour to about 48 hours, or about 1 hour to about 24 hours, for example, about 1 hour.

The obtained crystalline form may be further isolated, e.g., by filtration.

Figure 19:
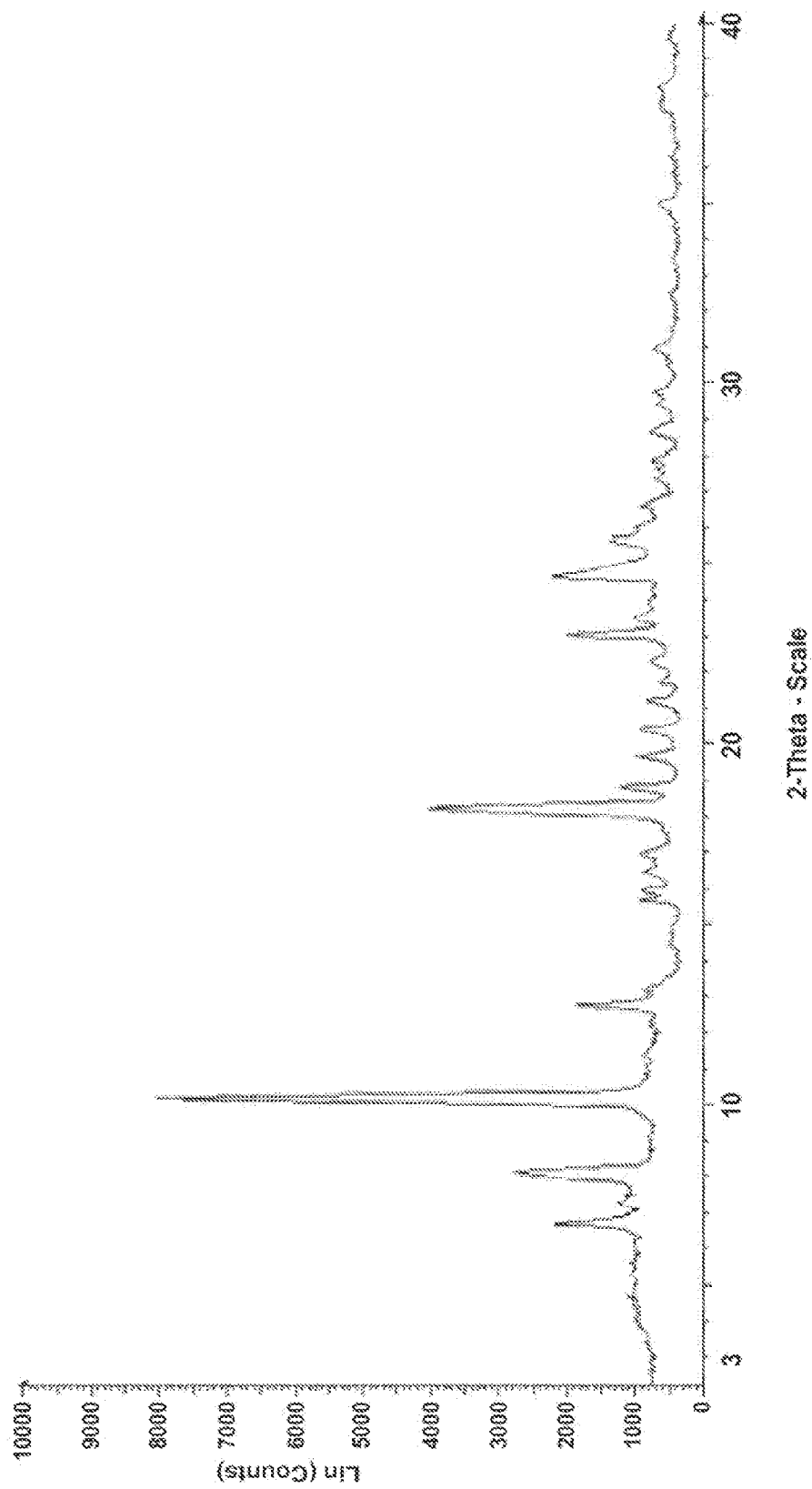
FIG. 19 shows an X-ray powder diffractogram of Febuxostat Form F7.
Figure 20:
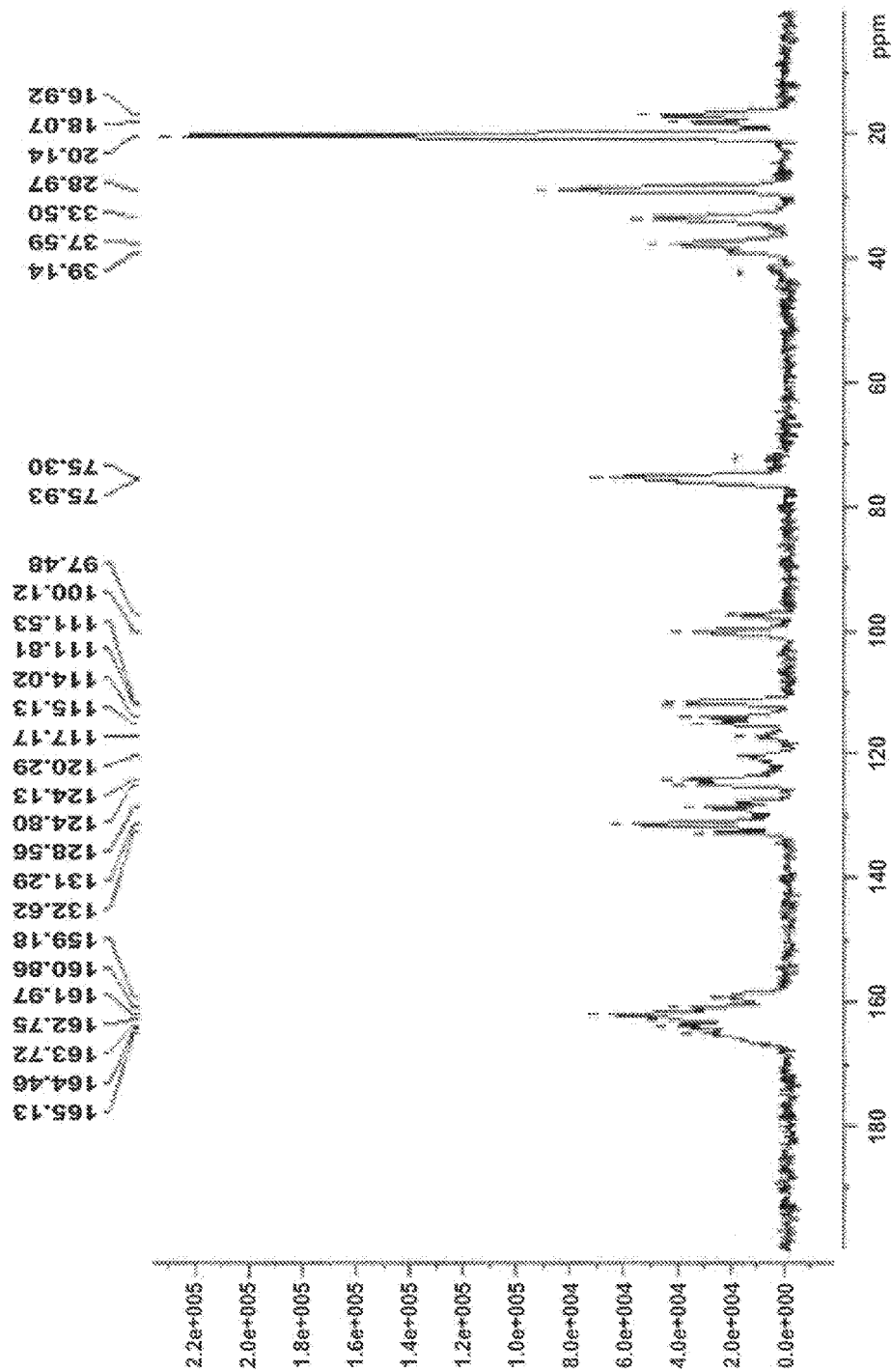
FIG. 20 shows a solid-state $^{13}$C NMR spectrum of Febuxostat Form F7 in the 0-200 ppm range.
Figure 21:
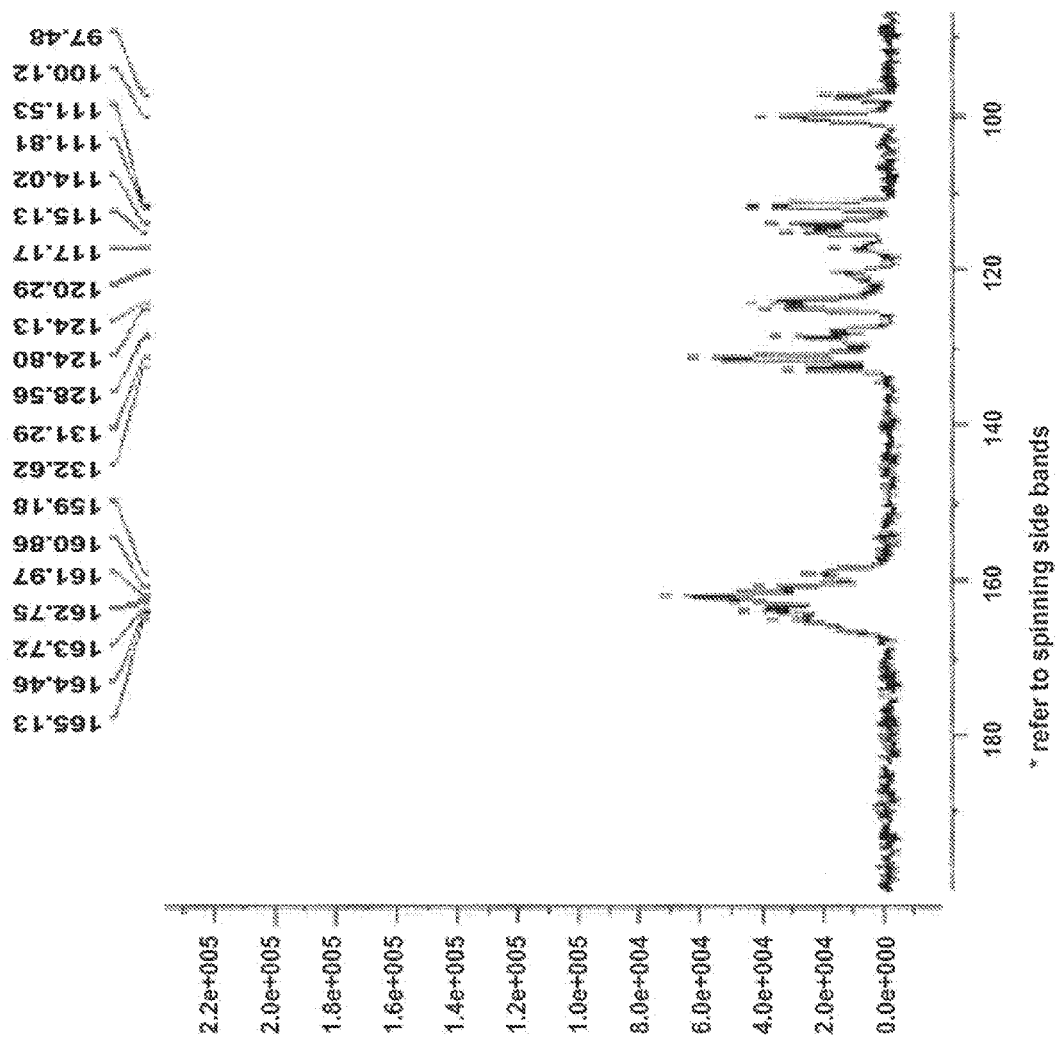
FIG. 21 shows a solid-state $^{13}$C NMR spectrum of Febuxostat Form F7 in the 100-200 ppm range.

The present invention encompasses crystalline Febuxostat, designated as Form F7. Form F7 can be characterized by data selected from: an X-ray powder diffraction pattern having peaks at 6.7°, 8.1°, 10.1°, 12.8°, and 18.2°±0.2° 2θ; an X-ray powder diffraction pattern substantially as depicted in FIG. 19; a solid-state $^{13}$C NMR spectrum with signals at 128.6, 131.3 and 162.7±0.2 ppm; a solid-state $^{13}$C NMR spectrum having chemical shifts differences between the signal exhibiting the lowest chemical shift and another in the chemical shift range of 100 to 180 ppm of 28.5, 31.3 and 62.6±0.1 ppm; a solid-state $^{13}$C NMR spectrum substantially as depicted in FIG. 20 or 21; and combinations thereof. The signal exhibiting the lowest chemical shift in the chemical shift area of 100 to 180 ppm is typically at 100.1±1 ppm. The Febuxostat Form F7 as defined in any of the above data, may be further characterized by additional XRPD peaks at 15.6°, 15.9°, 18.8°, 23.0°, and 24.7°±0.2° 2θ.

The present invention also encompasses a process for preparing Febuxostat Form F7 comprising crystallizing Febuxostat from a mixture comprising dimethylformamide ("DMF") and n-heptane. The crystallization, typically done at about room temperature, may comprise dissolving Febuxostat in DMF and then adding n-heptane to obtain said crystalline form. The process may further comprise a maintaining step wherein the mixture is maintained, e.g., at about room temperature, for a time such as about 1 hour to about 72 hours, or about 1 hour to about 48 hours, for example, about 43.5 hours.

Figure 22:
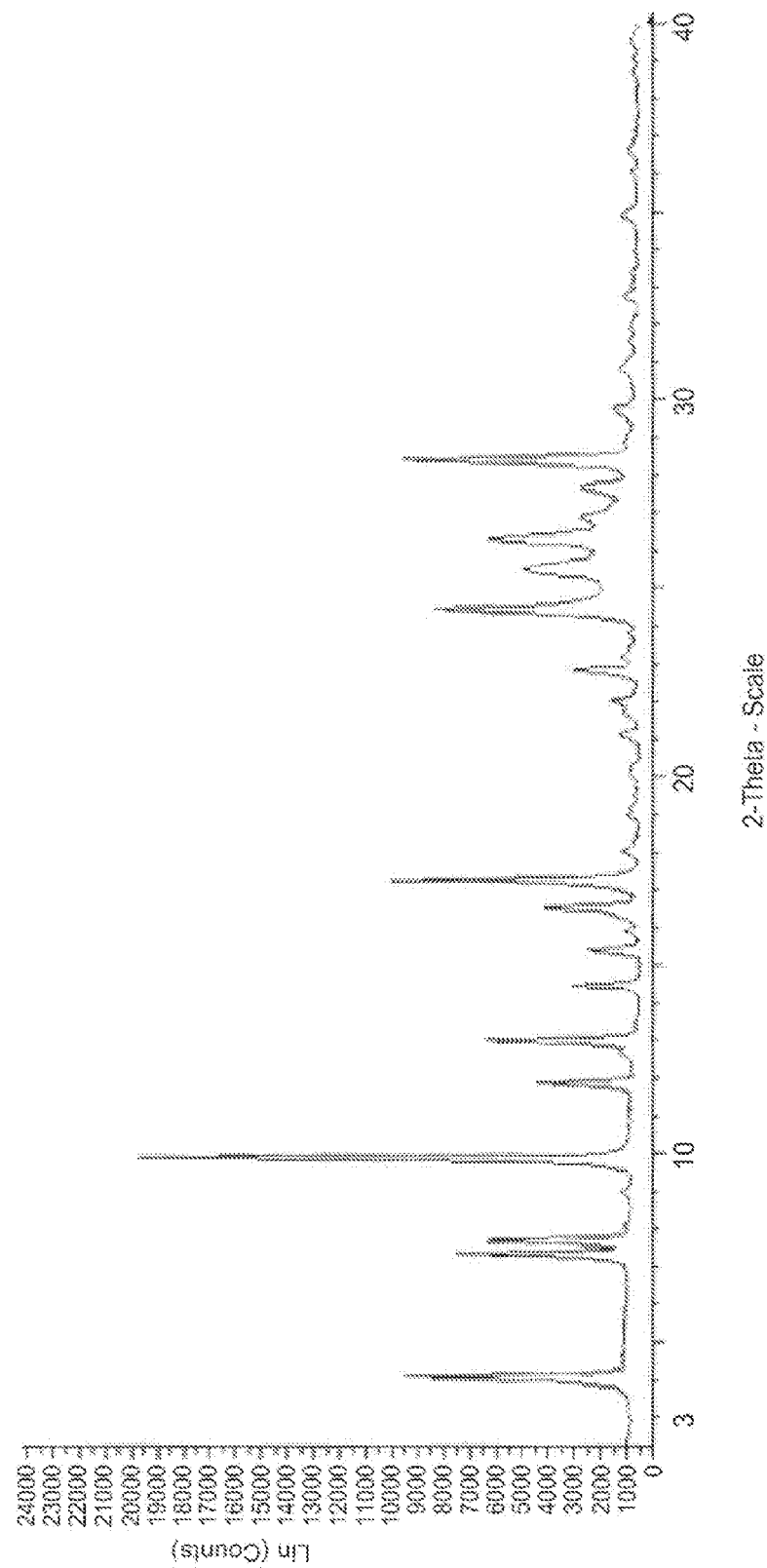
FIG. 22 shows an X-ray powder diffractogram of Febuxostat Form F8.
Figure 23:
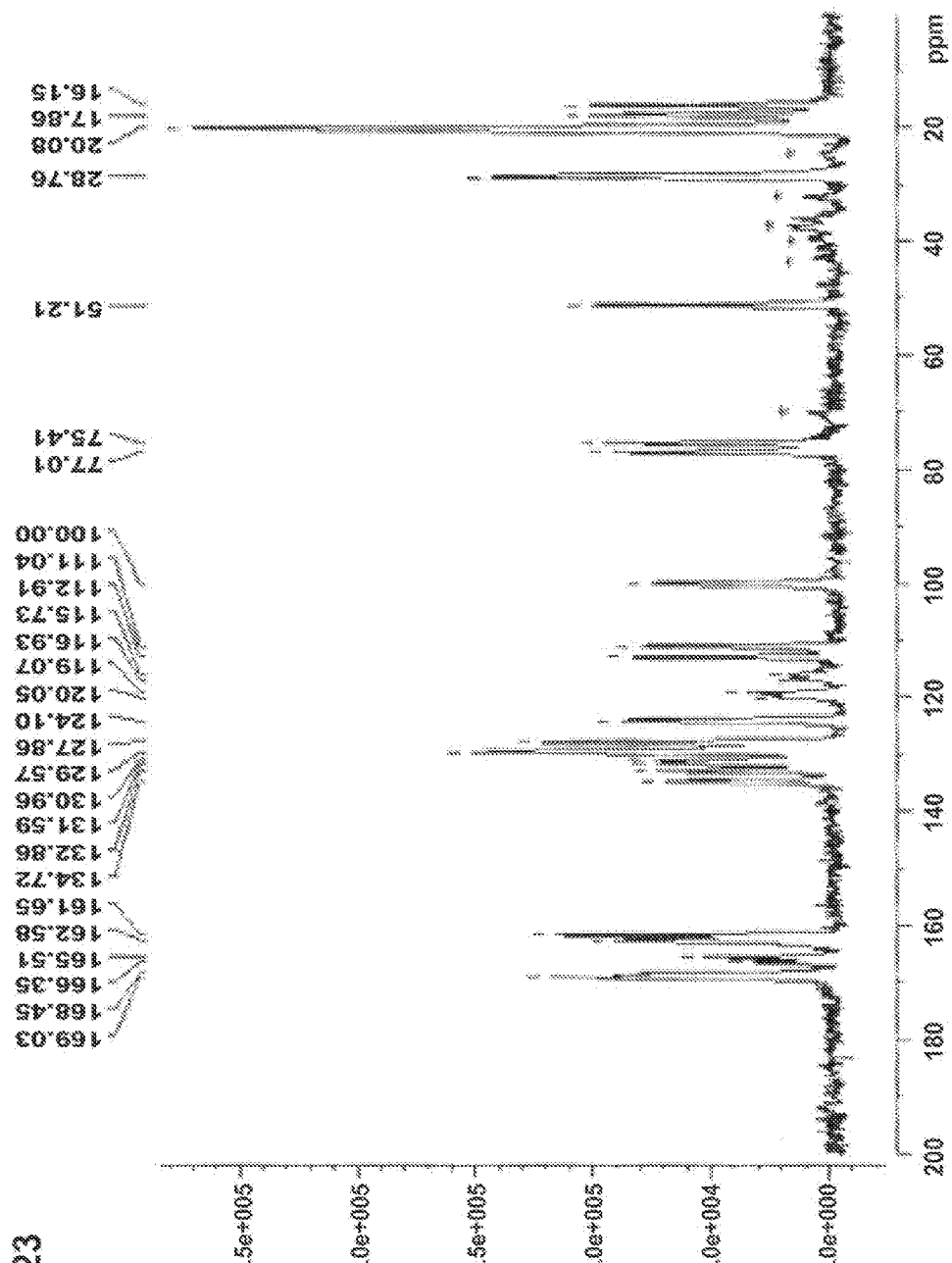
FIG. 23 shows a solid-state $^{13}$C NMR spectrum of Febuxostat Form F8 in the 0-200 ppm range.
Figure 24:
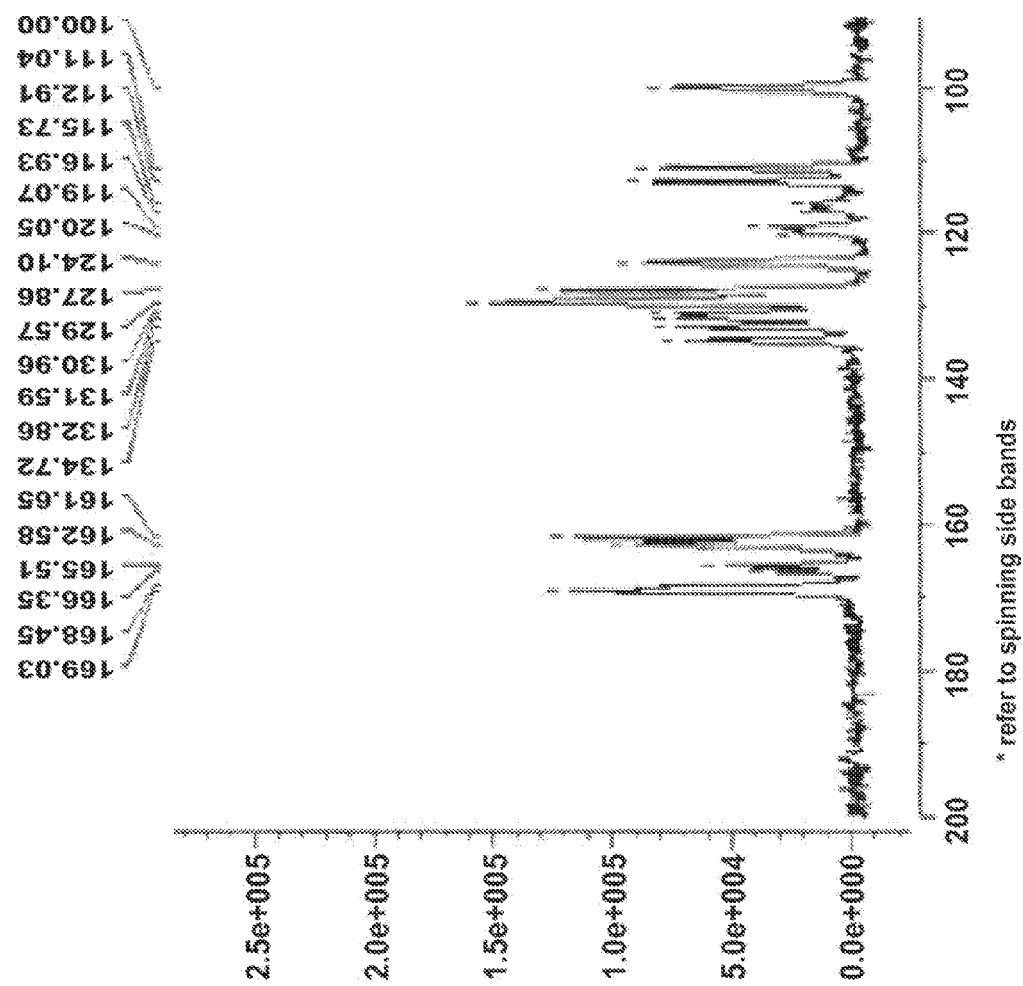
FIG. 24 shows a solid-state $^{13}$C NMR spectrum of Febuxostat Form F8 in the 100-200 ppm range.

The present invention encompasses crystalline Febuxostat designated as Form F8. Form F8 can be characterized by data selected from: an X-ray powder diffraction pattern having peaks at 4.0°, 7.3°, 7.7°, 9.9° and 17.3°±0.2° 2θ; an X-ray powder diffraction pattern substantially as depicted in FIG. 22; a solid-state $^{13}$C NMR spectrum with signals at 100.0, 127.9 and 134.7±2 ppm; a solid-state $^{13}$C NMR spectrum having chemical shifts differences between the signal exhibiting the lowest chemical shift and another in the chemical shift range of 100 to 180 ppm of 0.0, 27.9 and 34.7±0.1 ppm; a solid-state $^{13}$C NMR spectrum substantially as depicted in FIG. 23 or 24 and combinations thereof. The signal exhibiting the lowest chemical shift in the chemical shift area of 100 to 180 ppm is typically at 100.0±1 ppm. The Febuxostat Form F8 as defined in any of the above data, may be further characterized by additional XRPD peaks at 11.9°, 13.0°, 14.5°, 16.5° and 24.4°±0.2° 2θ.

The present invention encompasses a process for preparing Febuxostat Form F8 comprising slurrying Febuxostat form F3 in methyl benzoate. The slurrying may be done at a temperature such as about room temperature. A maintaining step may be done, wherein the slurry may be maintained, e.g., at about room temperature, for about 1 hour to about 48 hours, for example, for about 25 hours.

The obtained crystalline form may be further isolated, e.g., by filtration. The isolated crystalline form may further be dried.

Figure 25:
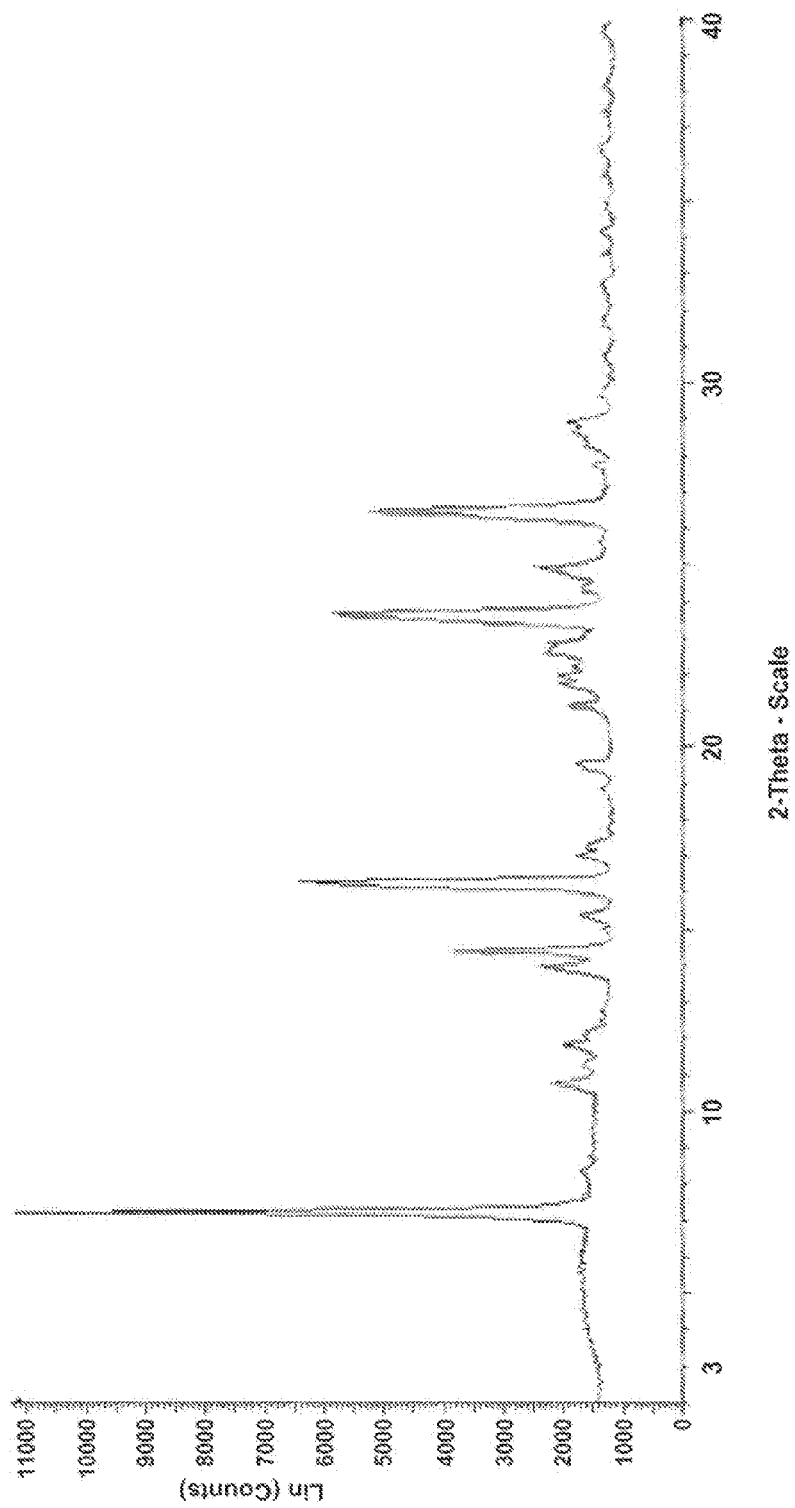
FIG. 25 shows an X-ray powder diffractogram of Febuxostat Form F9.
Figure 26:
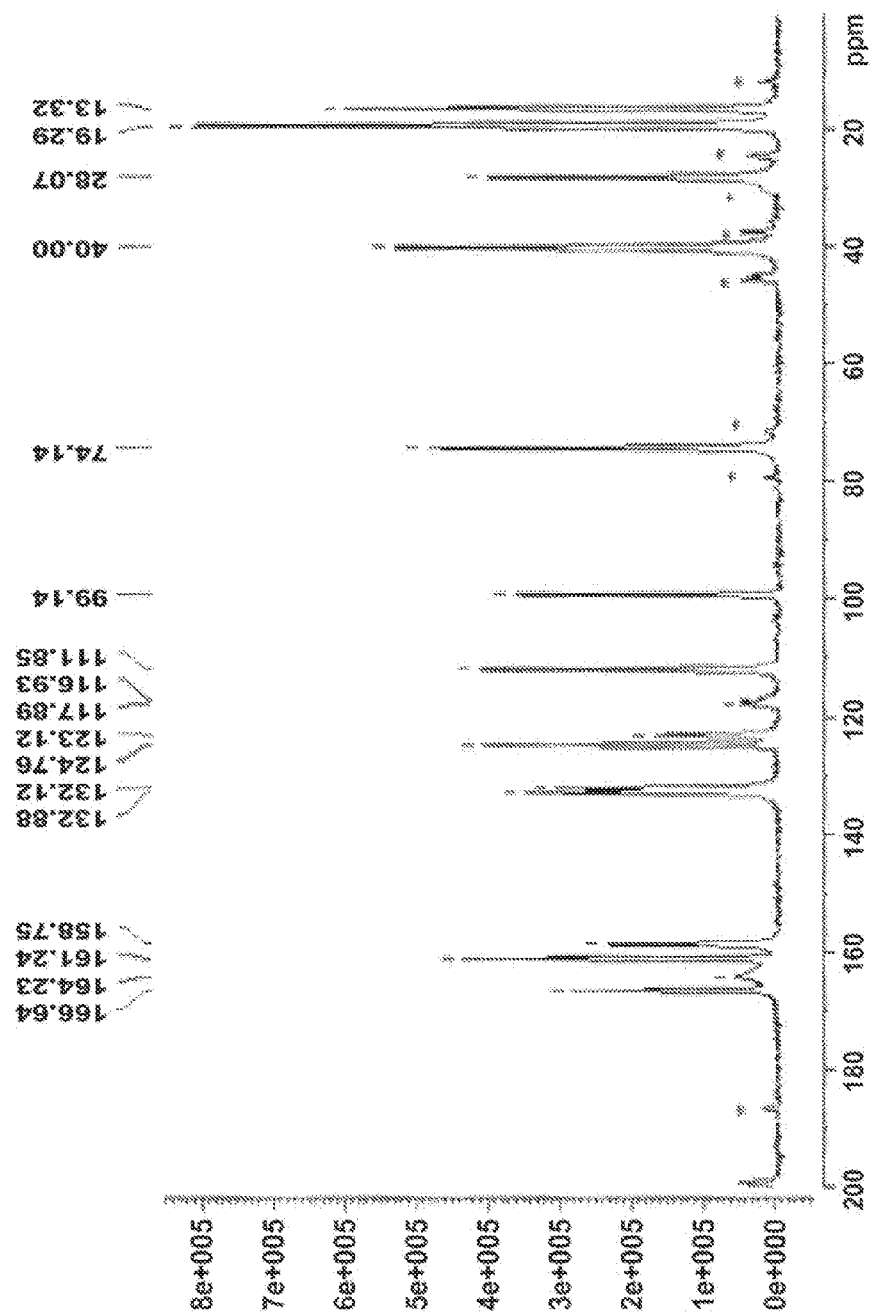
FIG. 26 shows a solid-state $^{13}$C NMR spectrum of Febuxostat Form F9 in the 0-200 ppm range.
Figure 27:
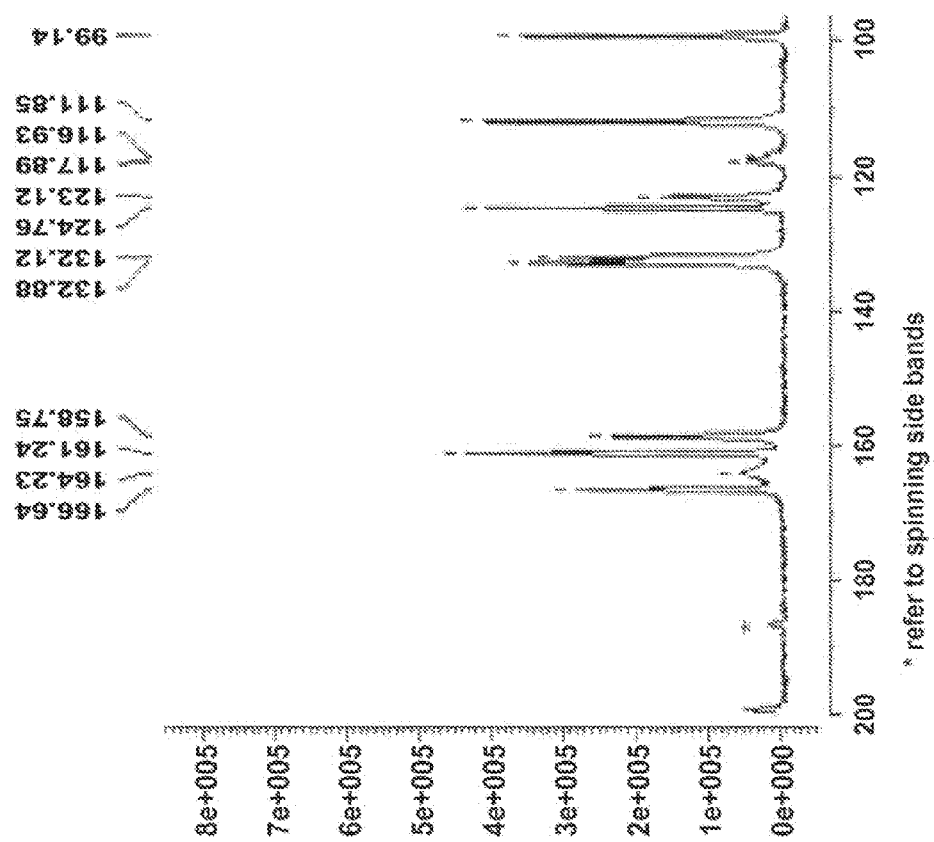
FIG. 27 shows a solid-state $^{13}$C NMR spectrum of Febuxostat Form F9 in the 100-200 ppm range.

The present invention encompasses crystalline Febuxostat, designated as Form F9. Form F9 can be characterized by data selected from: an X-ray powder diffraction pattern having peaks at 7.2°, 10.7°, 14.0°, 14.4° and 16.3°±0.2° 2θ; an X-ray powder diffraction pattern substantially as depicted in FIG. 25; a solid-state $^{13}$C NMR spectrum with signals at 123.1, 124.8 and 132.8±0.2 ppm; a solid-state $^{13}$C NMR spectrum having chemical shifts differences between the signal exhibiting the lowest chemical shift and another in the chemical shift range of 100 to 180 ppm of 11.2, 12.9 and 20.9±0.1 ppm; a solid-state $^{13}$C NMR spectrum substantially as depicted in FIG. 26 or 27; and combinations thereof. The signal exhibiting the lowest chemical shift in the chemical shift area of 100 to 180 ppm is typically at 111.9±1 ppm. The Febuxostat Form F9 as defined in any of the above data, may be further characterized by additional XRPD peaks at 11.9°, 17.0°, 19.5°, 23.7° and 26.5°±0.2° 2θ.

The present invention encompasses a process for preparing Febuxostat Form F9 comprising slurrying Febuxostat form F3 in dimethylsulfoxide ("DMSO"). The slurrying may be done at a temperature such as about room temperature. The process may further comprise a maintaining step for a time such as about 1 hour to about 48 hours, for example, about 46 hours. The obtained crystalline form may be further isolated, e.g., by filtration.

Figure 28:
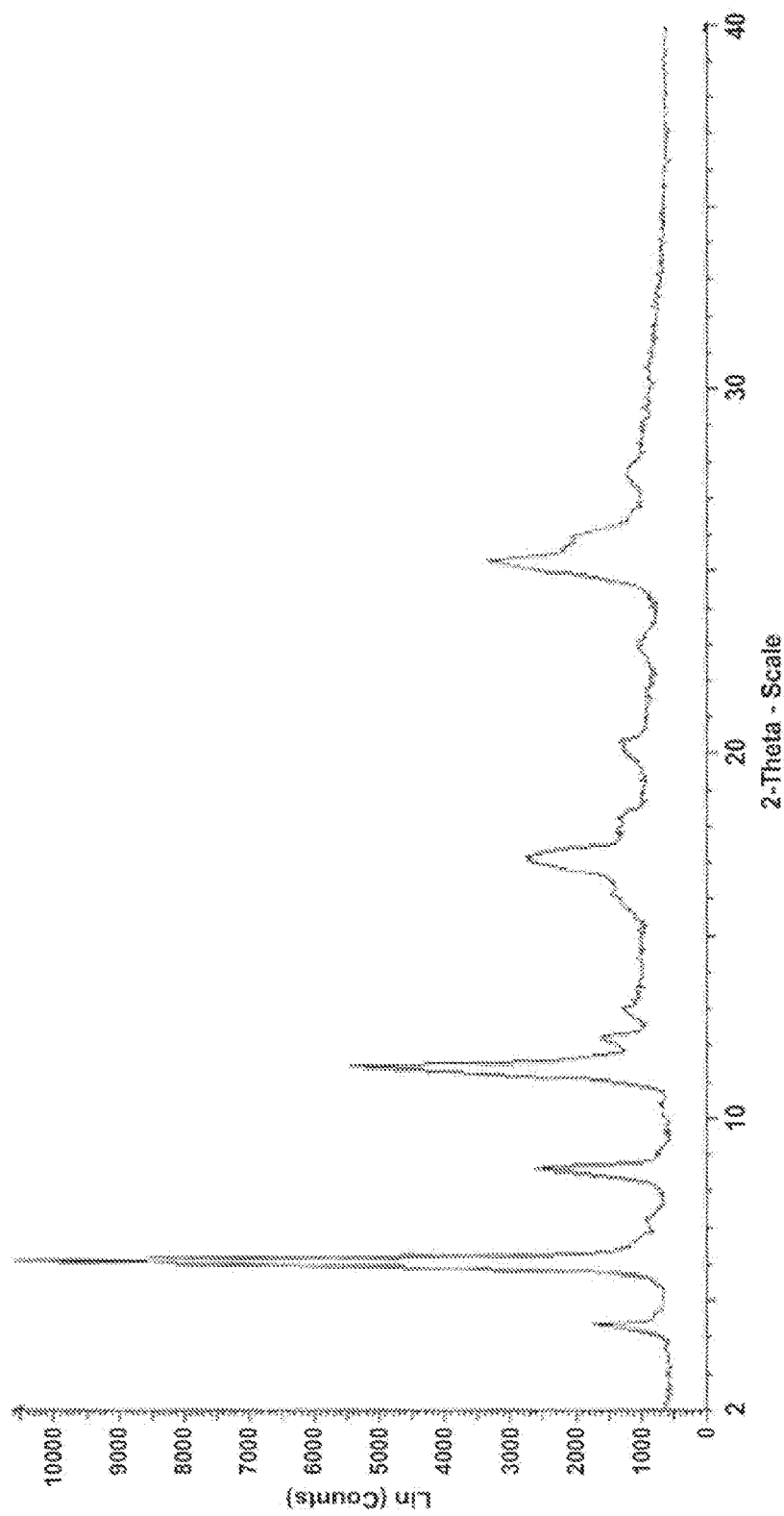
FIG. 28 shows an X-ray powder diffractogram of Febuxostat Form F11.

The present invention encompasses crystalline Febuxostat, designated as form F11. Form F11 can be characterized by data selected from: an X-ray powder diffraction pattern having peaks at: 4.3°, 6.0°, 8.6°, 11.4° and 12.2°±0.2° 2θ; an X-ray powder diffraction pattern substantially as depicted in FIG. 28; and a combination thereof. Febuxostat form F11 as defined in any of the above data, may further be characterized by additional XRPD peaks at 17.0° and 25.4°±0.2° 2θ.

The present invention also encompasses a process for preparing Febuxostat Form F11 comprising precipitating Febuxostat from tert-butanol. The precipitation may comprise dissolving Febuxostat in tert-butanol; and lyophilizing to obtain febuxsostate crystalline form F11. The dissolving step may be done by heating to a temperature such as from about 35° C. to about 82° C. or from about 35° C. to about 40° C. Lyophilization is typically done by a process comprising cooling the solution to obtain a frozen mixture, and evaporating the solvent while maintaining the mixture frozen at low temperatures. The lyophilizing step may be done under vacuum, at a pressure of from about 2 mm Hg to about 14.8 mm Hg. The cooling may be done to a temperature such as from about 0° C. to about −50° C. or from about −6° C. to about −42° C.

Figure 29:
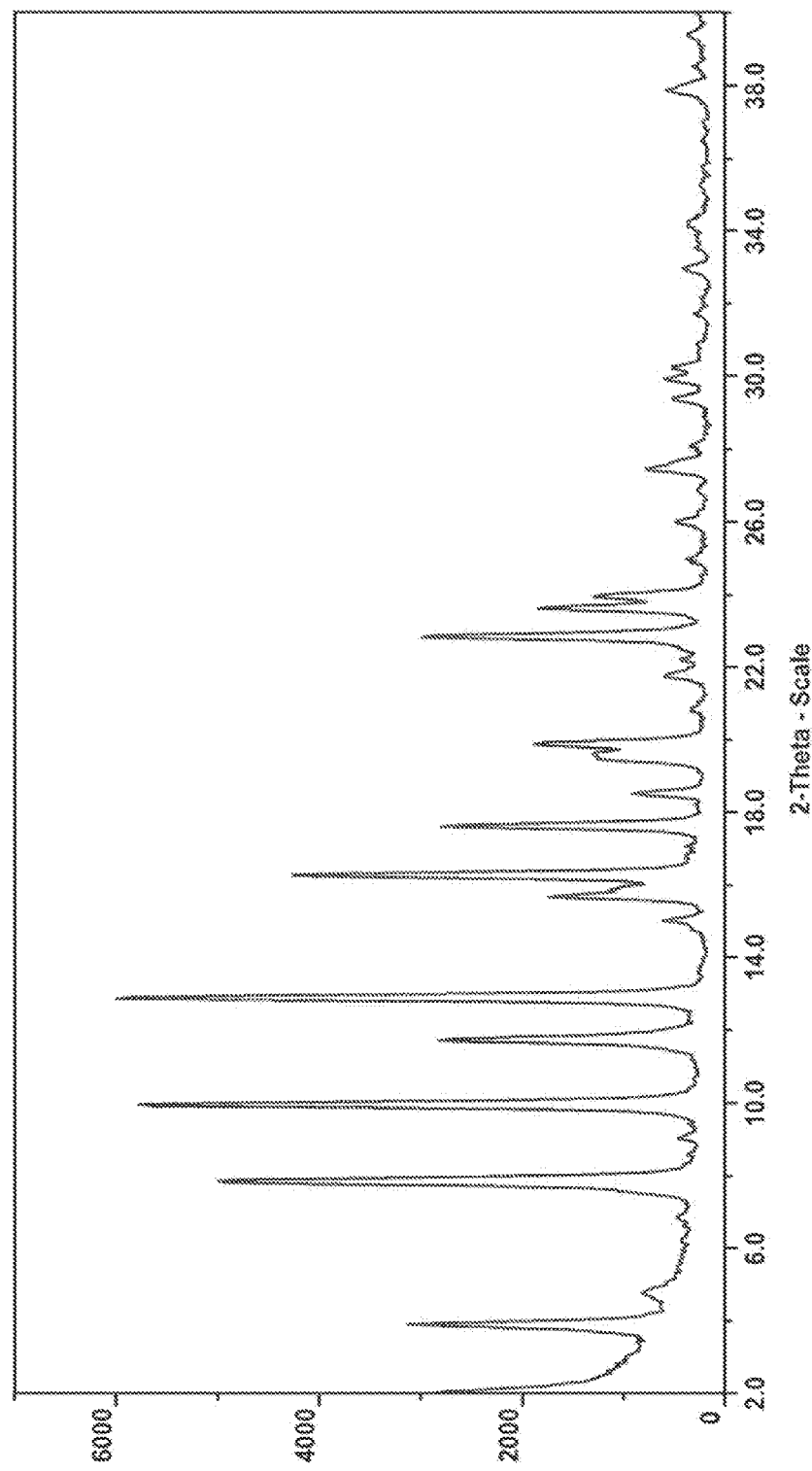
FIG. 29 shows an X-ray powder diffractogram of Febuxostat form F12.

The present invention encompasses crystalline Febuxostat, designated as form F12. Form F12 can be characterized by data selected from: an X-ray powder diffraction pattern having peaks at: 3.9°, 7.9°, 10.0°, 11.7° and 12.9°±0.2° 2θ; an X-ray powder diffraction pattern substantially as depicted in FIG. 29; and a combination thereof. The Febuxostat form F12 as defined in any of the above data, may further be characterized by additional XRPD peaks at 15.7°, 16.2°, 17.6°, 19.9° and 22.8°±0.2° 2θ.

Figure 30:
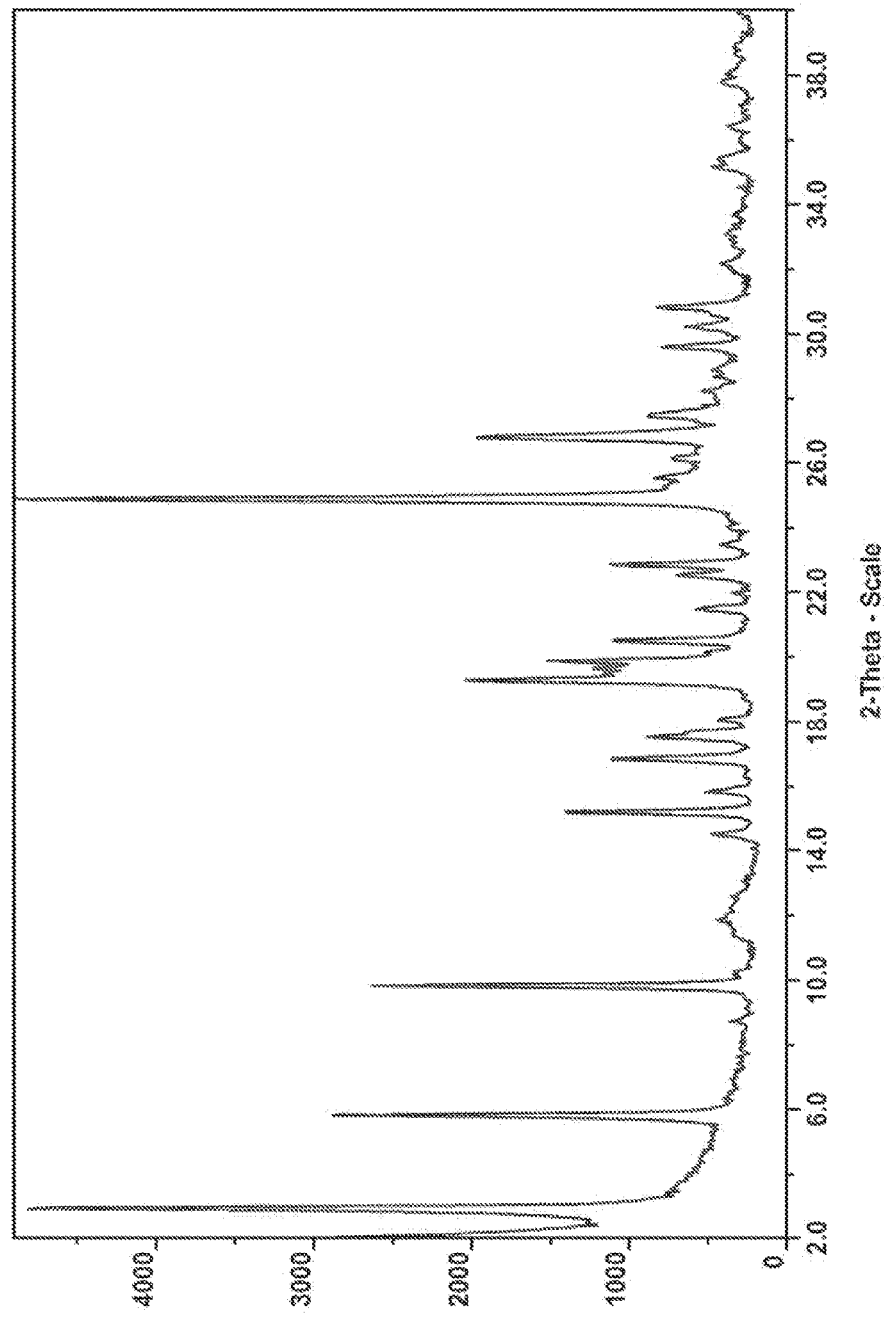
FIG. 30 shows an X-ray powder diffractogram of Febuxostat Form F13.

The present invention also encompasses a process for preparing Febuxostat Form F12 comprising crystallizing Febuxostat from a mixture of dioxane and water. The crystallization may comprise dissolving Febuxostat in dioxane at about room temperature; and adding water to obtain said crystalline form. The process may further comprise a maintaining step at a temperature such as about room temperature, for a time of about 1 hour to about 12 hours, for example, for about 2 hours. The obtained crystalline form may be further isolated, e.g., by filtration.

the present invention encompasses crystalline Febuxostat, designated as form F13. Form F13 can be characterized by data selected from: and X-ray powder diffraction pattern having peaks at 2.9°, 5.8°, 9.8°, 15.2° and 19.2°±0.2° 2θ; an X-ray powder diffraction pattern substantially as depicted in FIG. 30; and combinations thereof. The Febuxostat form F13 as defined in any of the above data, may further by characterized by additional XRPD peaks at 16.8°, 17.5°, 19.9°, 20.4° and 22.8°±0.2° 2θ.

The present invention encompasses a process for preparing Febuxostat Form F13 comprising crystallizing Febuxostat form chloroform. The crystallization may comprise dissolving Febuxostat in chloroform to obtain a mixture; precipitating the Febuxostat; and isolating the obtained precipitate. The precipitating may be done by adding a $C_5$-$C_8$ hydrocarbon, such as n-heptane or n-hexane to the reaction mixture or by heating; cooling; and optionally maintaining the mixture. The heating may be done to a temperature such as about the reflux temperature for a time of about 1 min to about 1 hr, or for about 20 minutes. The cooling may be done to a temperature such as about 40° C. to about 0° C., or about room temperature. The maintaining is typically done at a temperature of at about 0° C. to about 40° C. for a time such as about 1 min to about 24 hours, for example, for about 1.258 hours. The isolation of the precipitate may be done by filtering.

Figure 31:
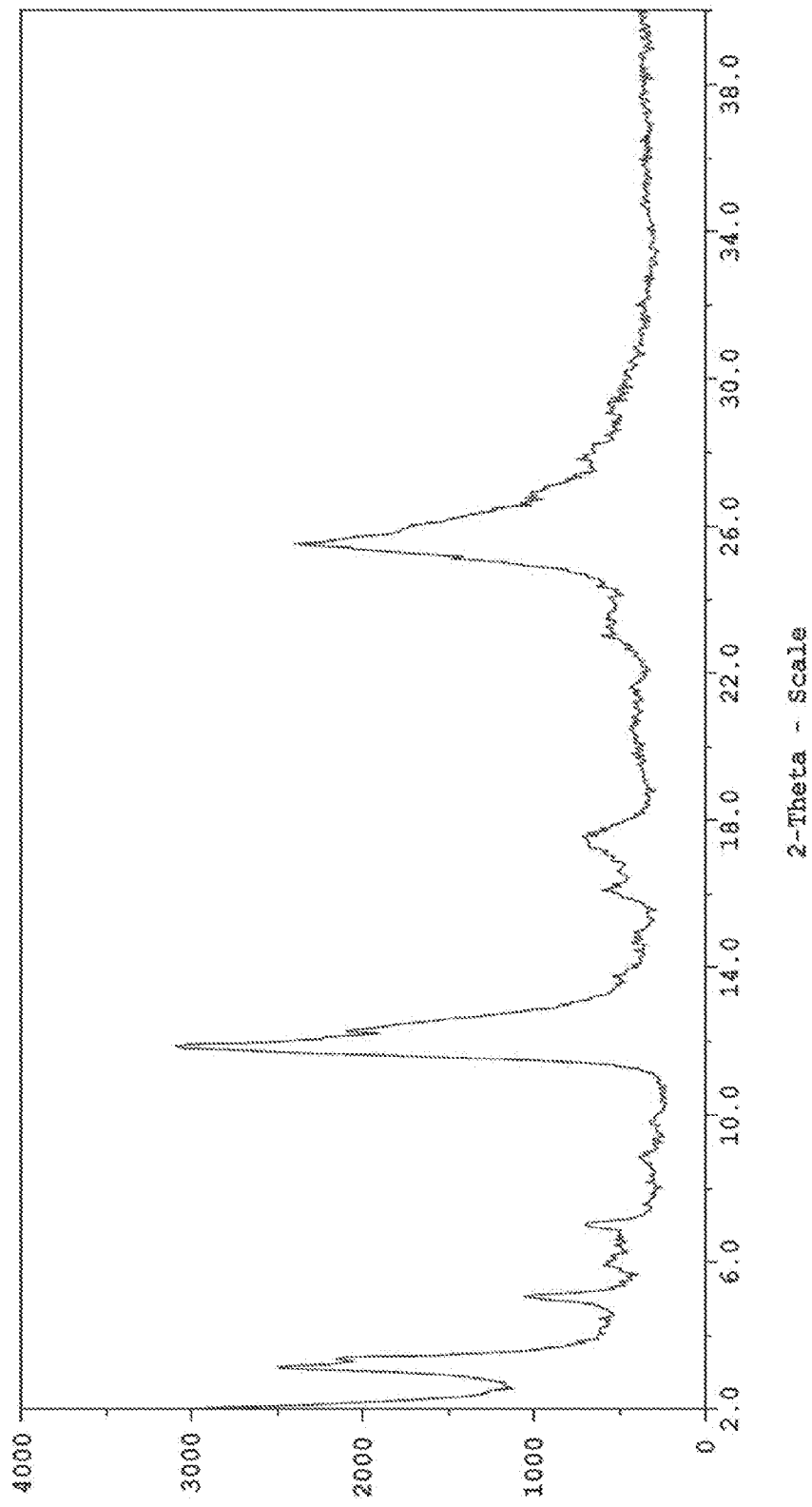
FIG. 31 shows an X-ray powder diffractogram of Febuxostat Form F14.

The present invention encompasses crystalline Febuxostat, designated as form F14. form F14 can be characterized by data selected from: an X-ray powder diffraction pattern having peaks at: 3.2°, 5.1°, 7.0°, 11.8° and 25.5°±0.2° 2θ; an X-ray powder diffraction pattern substantially as depicted in FIG. 31; and combinations thereof.

The present invention also encompasses a process for preparing Febuxostat form F14 comprising crystallizing Febuxostat from a mixture comprising chloroform and a $C_5$-$C_8$ hydrocarbon or water. The crystallization may comprise dissolving Febuxostat in chloroform; and adding a solvent selected from: water and a $C_5$-$C_8$ hydrocarbon to obtain said crystalline form. Suitable $C_5$-$C_8$ hydrocarbons include, for example, n-heptane and n-hexane.

The process may further comprise maintaining the mixture, e.g., at about room temperature, for a time such as about 1 hour to about 24 hours, or about 1 hour to about 5 hours. The obtained crystalline form may be further isolated, e.g., by filtering and drying.

The above crystalline forms of Febuxostat can be used in the preparation of a pharmaceutical composition comprising any one, or combinations of, the forms of Febuxostat described above, and at least one pharmaceutically acceptable excipient.

The present invention further provides 1) a pharmaceutical composition comprising any one, or combination, of Febuxostat crystalline Forms described above and a pharmaceutically acceptable excipient; 2) the use of any one of the above pharmaceutical compositions for the treatment hyperuricemia in patients with gout and 3) methods of treatment of a patient with gout, comprising administering to said patient an effective amount of a pharmaceutical composition comprising any one, or combinations of the forms of Febuxostat described herein.

The pharmaceutical composition of the present invention can be in a solid or liquid form. If the pharmaceutical composition is in a liquid form, the one, or combination, of the Febuxostat crystalline Forms described above are retained as solid(s) in the liquid pharmaceutical composition, e.g., as a suspension.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Instrumentation

X-Ray Powder Diffraction:

The X-ray powder diffraction was performed on a Bruker X-ray powder diffractometer model D8 advance equipped with a lynx eye detector or an ARL powder diffractometer model XTRA-019, equipped with round standard aluminum sample holder with round zero background quartz plate. The scanning parameters used were: Copper Kα1 radiation. (λ=1.5418 Å), range: 2-40 degrees 2θ; scan mode: continuous scan.

The peak positions were determined by using silicon powder as internal standard in an admixture with the sample measured. The position of the silicon (111) peak was corrected to be 28.45 degrees two theta. The positions of the peaks were corrected respectively (no corrections were performed on the presented diffractograms in the figures). $^{13}C$ NMR spectra:

$^{13}C$ NMR at 125 MHz using Bruker Avance II+ 500. SB probe using 4 mm rotors

Magic angle was set using KBr. Homogeneity of magnetic field checked using adamantane. Parameters for Cross polarization optimized using glycine.

Spectral reference set according to glycine as external standard (176.03 ppm for low field carboxyl signal).

Magic Angle Spinning Rate: 11 kHz

Pulse Program: cp with tppm15 during decoupling

Delay time: 5 s (except for Forms F7, F8 and F9 of Febuxostat, wherein the delay time was 2 s)

Contact time: 2 msec.

Number of Scans: 1024 (except for Forms F8 and F9 of Febuxostat, wherein the number of scans was 2048)

The term "V" relates to ml of solvent or antisolvent per g of starting material febuxostat.

EXAMPLES

Example 1

Preparation of Febuxostat Form F1

Febuxostat (1 g) was placed in a 50 ml round bottom flask equipped with a magnetic stirrer and a reflux condenser. Methylisobutylketone (MIBK) (10 ml) was added and the resulting mixture was heated to reflux using an oil bath to give clear yellowish solution. Then, the heating was stopped, the oil bath was removed and the mixture was allowed to cool to RT and stirred at RT for 1.5 h. A white precipitate formed during the cooling. The mixture was then filtered and the separated solid was washed with MIBK (1 ml) to provide a wet white solid (0.64 g). A portion (0.44 g) was dried in vacuo at 50° C. over 22.5 h to provide the product as a white solid (0.33 g).

Example 2

Preparation of Febuxostat Form F2

Febuxostat (1 g) was placed in a 250 ml round bottom flask equipped with a magnetic stirrer. Methylethylketone (MEK) (35 ml, 35V) was added and the resulting mixture was stirred at RT to give a clear yellowish solution. N-heptane (175 ml) was added and the resulting solution was stirred at RT over 20 h. The mixture was then filtered to provide a wet white solid (1.03 g), which was then dried in vacuo at 40° C. over 24 h to give white solid (0.43 g).

Example 3

Preparation of Febuxostat Form F2

Febuxostat (0.5 g) was placed in a 250 ml round bottom flask equipped with a magnetic stirrer. Acetone (11.5 ml, 23V) was added and the resulting mixture was stirred at RT to give a clear yellowish solution. n-Heptane (126.5 ml, 253V) was added and the resulting solution was stirred at RT over 16.25 h. The mixture was then filtered to provide a wet white solid (0.31 g). The solid was dried in vacuo at 50° C. over 22 h to provide a white solid (0.23 g).

Example 4

Preparation of Febuxostat Form F2

A mixture of Febuxostat (0.5 g) and acetone (12.5 ml, 25V) was prepared to obtain yellow solution. n-Hexane (75 ml, 1.50V) was added to the solution and a white suspension was formed. The suspension was stirred for 3 h at 25° C., whereupon it was filtered. The filtered solid was analyzed by XRD and form F2 was obtained.

Example 5

Preparation of Febuxostat Form F2

A mixture of Febuxostat (0.5 g) and acetone (12.5 ml, 25V) was prepared to obtain a yellow solution. n-Hexane (75 ml, 150V) was added to the solution and a white suspension was formed. The suspension was stirred for 3 h at 25° C., whereupon it was filtered. The filter cake thus obtained was dried 16 h at 50° C. The solid was analyzed by XRD and form F2 was obtained.

Example 6

Preparation of Febuxostat Form F2

Febuxostat crystalline form F3 (1.00 g) was placed in a 50 ml round bottom flask equipped with a magnetic stirrer. DCM (15 ml, 3.5V) was added and the resulting mixture (a white slurry) was stirred at RT for 25 h. The mixture was then filtered to provide a wet white solid (0.81 g). A portion (0.15 g) of the wet solid was taken for polymorphism analysis and was identified as Febuxostat Form F2, and the rest was dried in vacuo at 50° C. over 18 h to provide a white solid (0.50 g).

Example 7

Preparation of Febuxostat Form F3

A mixture of Febuxostat (96 g) and EtOH (770 ml, 8V) was heated to 78° C. to form a yellow solution. The solution was then cooled to 5° C. and an off-white suspension was obtained. The suspension was stirred for 1 h at 5° C., whereupon it was filtered. The filter cake thus obtained was dried 16 h at 40° C.

Example 8

Preparation of Febuxostat Form F4

Febuxostat F3 (0.50 g) was placed in a 50 ml round bottom flask equipped with a magnetic stirrer. Acetic-acid ("AcOH") (7.5 ml, 15V) was added and the mixture (a white slurry) was stirred at RT over 25 h. The mixture was then filtered to give a wet white solid (0.49 g). The wet solid was analyzed by XRD.

Example 9

Preparation of Febuxostat Form F4

Febuxostat (0.50 g) was placed in a 50 ml round bottom flask equipped with a magnetic stirrer and a reflux condenser. AcOH (10 ml, 20V) was added while heating to reflux on an oil bath, to give a clear yellowish solution. Then the heating was stopped, the oil bath was removed and the mixture was allowed to cool to RT. After 3.5 h of stirring at RT, a wet white solid (0.51 g) was collected by filtration. The wet solid was analyzed by XRD.

Example 10

Preparation of Febuxostat Form F5

Febuxostat (0.50 g) was placed in a 100 ml round bottom flask equipped with a magnetic stirrer. Dimethylacetamide ("DMA") (0.5 ml, 1V) was added and the mixture was stirred at RT to give a clear yellowish solution. n-Heptane (10 ml, 20V) was added, and the resulting clear mixture was stirred at RT over 43 h. During this time a precipitate formed. The precipitate was separated by filtration to provide a wet solid. The wet solid was analyzed by XRD.

Example 11

Preparation of Febuxostat Form F6

A mixture of Febuxostat (0.5 g) and chloroform (4.5 ml, 9V) was heated to 61° C. (reflux) to obtain yellow solution. The solution was then cooled to 25° C. and a white suspension was obtained. The suspension was then stirred for 1 h at 25° C., whereupon it was filtered. The filtered solid was analyzed by XRD.

Example 12

Preparation of Febuxostat Form F7

Febuxostat (0.50 g) was placed in a 100 ml round bottom flask equipped with a magnetic stirrer. Dimethylformamide ("DMF") (1 ml, 2V) was added and the mixture was stirred at RT to give a clear yellowish solution. n-Heptane (20 ml, 40V) was added and the resulting clear mixture wax stirred at RT over 43.5 h. During this time a precipitate formed. The precipitate was separated by filtration to provide a wet solid. The wet solid was analyzed by XRD.

Example 13

Preparation of Febuxostat Form F8

Febuxostat form F3 (0.50 g) was placed in a 20 ml vial equipped with a magnetic stirrer. Methyl benzoate (5 ml, 10V) was added, and the mixture (a white slurry) was stirred at RT over 25 h. During this time a precipitate formed. The precipitate was separated by filtration to provide a wet solid (1.35 g). The solid was dried in vacuo at 50° C. over 17 h to give a white solid (0.34 g).

Example 14

Preparation of Febuxostat Form F9

Febuxostat form F3 (0.50 g) was placed in a 20 ml vial equipped with a magnetic stirrer. Dimethylsulfoxide ("DMSO") (2.5 ml, 5V) was added, and the mixture was stirred at RT over 46 h. During this time a precipitate formed. The precipitate was separated by filtration to provide a wet solid (0.27 g). The wet solid was analyzed by XRD.

Example 15

Preparation of Febuxostat Form F10

Febuxostat (20.00 g) was placed in a 1 L round bottom flask equipped with a magnetic stirrer and a reflux condenser. MIBK (200 ml, 10V) was added. The mixture was heated to reflux on an oil bath and stirred at reflux for 5 min to form a solution. n-Heptane (300 ml, 15V) was added to the clear yellowish solution, in portions during 10 min and a white precipitate formed. Then, the heating was stopped and the mixture was allowed to cool and stir at RT for 1.5 h. A wet white solid formed and was collected (32.36 g) by filtration. The sample was dried in vacuo at 50° C. over 24 h to give white solid (17.07 g).

Example 16

Preparation of Febuxostat Form F10

Febuxostat (5.09 g) was placed in a 500 ml round bottom flask equipped with a magnetic stirrer and a reflux condenser. MIBK (50 mL 10V) was added. The mixture was heated to reflux on an oil bath and stirred at reflux for 5 min. N-hexane (150 ml, 30V) was added to the resulted clear yellowish solution, in portions during 10 min and a white precipitate was formed. Then the heating was stopped and the mixture was allowed to cool and stir at RT during 1 h. A wet white solid formed and was collected (5.04 g) by filtration. The sample was dried in vacuo at 50° C. over 23.5 h to give white solid (4.15 g).

Example 17

Preparation of Febuxostat Form F11

Febuxostat (5.00 g) was dissolved in tert-butanol (500 g) at 35° C.-40° C. The clear colorless solution was lyophilized at −42° C.-(−6° C.) under vacuum of 2-14.8 mmMg for 24 h. A bulky white solid was collected (5.5 g).

Example 18

Preparation of Febuxostat Form F12

Febuxostat (1.00 g) was dissolved in dioxane (8 ml, 8V) in a 100 ml round bottom flask equipped with a magnetic stirrer. Tap water (8 ml, 8V) was added to the clear solution and a white precipitate formed. The mixture was stirred at RT over 2 h. During this time a precipitate formed. The precipitate was separated by filtration to provide a wet solid (2.43 g).

Example 19

Preparation of Febuxostat Form F13

Febuxostat (5.00 g) was dissolved in CHCl$_3$ (250 ml, 50V) at about 25° C. in a 1 L round bottom flask equipped with magnetic stirrer. n-Hexane (250 ml, 50V) was added to form white precipitation. The obtained mixture was stirred during additional 2.5 hours at about 25° C. and filtered to give wet white solid (7.15 g).

Example 20

Preparation of Febuxostat Form F13

A mixture of Febuxostat (5.00 g) and ChCl$_3$ (55 ml, 11V) was heated to reflux on an oil bath in a 250 ml round bottom flask equipped with magnetic stirrer and a reflux condenser. After 20 min of stirring at reflux, the heating was stopped, the oil bath was removed and the mixture was allowed to cool and stir at RT over 1.25 h. A white precipitate formed during the cooling. The mixture was filtered to give wet white solid (4.70 g).

Example 21

Preparation of Febuxostat Form F14

Febuxostat (1.00 g) was dissolved in CHCl$_3$ (50 ml, 50V) in a 500 ml round bottom flask equipped with a magnetic stirrer. To the clear yellowish solution, n-heptane (50 ml, 50V) was added and a white precipitate formed. The mixture was stirred at RT over 2.5 h, and then it was filtered to provide a wet white solid (0.65 g). The solid was dried in vacuo at 50° over 23 h to give a white solid (0.24 g).

Example 22

Preparation of Febuxostat Form F14

Febuxostat (1.00 g) was dissolved in CHCl$_3$ (50 ml, 50V) in a 500 ml round bottom flask equipped with a magnetic stirrer. n-Hexane (50 ml, 50V) was added to the clear yellowish solution and a white precipitate formed. The mixture was stirred at RT for 2.5 h, and then it was filtered to give a wet white solid (1.28 g). The solid was dried in vacuo at 50° C. over 23 h to give a white solid (0.55 g).

Example 23

Preparation of Febuxostat Form F14

Febuxostat (1.00 g) was dissolved in CHCl$_3$ (50 ml, 50V) in a 1 L round bottom flask equipped with magnetic stirrer. Tap water (50 ml, 50V) was added to the clear yellowish solution and a white precipitate formed. The mixture was stirred at RT over 2.5 h, and then it was filtered to give 0.72 g of wet white solid. The solid was dried in vacuo at 50° C. over 23 h to give a white solid (0.15 g).

What is claimed:

1. A crystalline form of Febuxostat, designated Form F8, characterized by an X-ray powder diffraction pattern having peaks at 4.0°, 7.3°, 7.7°, 9.9° and 17.3°±0.2° 2θ.

2. The crystalline form of Febuxostat according to claim 1, further characterized by data selected from one or more of the following: an X-ray powder diffraction pattern substantially as depicted in FIG. 22; a solid-state $^{13}$C NMR spectrum with signals at 100.0, 127.9 and 134.7±0.2 ppm; a solid-state $^{13}$C NMR spectrum having chemical shifts differences between the signal exhibiting the lowest chemical shift and another in the chemical shift range of 100 to 180 ppm of 0.0, 27.9 and 34.7±0.1 ppm; a solid-state $^{13}$C NMR spectrum substantially as depicted in FIG. 23 or 24; additional XRPD peaks at 11.9°, 13.0°, 14.5°, 16.5° and 24.4°±0.2° 2θ; and combination thereof.

3. A crystalline form of Febuxostat, designated Form F9, characterized by an X-ray powder diffraction pattern having peaks at 7.2°, 10.7°, 14.0°, 14.4° and 16.3°±0.2° 2θ.

4. The crystalline form of Febuxostat, according to claim 3, farther characterized by data selected from one or more of the following: an X-ray powder diffraction pattern substantially as depicted in FIG. 25; a solid-state $^{13}$C NMR spectrum with signals at 123.1, 124.8 and 132.8±0.2 ppm; a solid-state $^{13}$C NMR spectrum having chemical shifts differences between the signal exhibiting the lowest chemical shift and another in the chemical shift range of 100 to 180 ppm of 11.2, 12.9 and 20.9±0.1 ppm; a solid-state $^{13}$C NMR spectrum substantially as depicted in FIG. 26 or 27; additional XRPD peaks at 11.9°, 17.0°, 19.5°, 23.7° and 26.5°±0.2° 2θ; and combinations thereof.

5. A crystalline form of Febuxostat, designated Form F11, characterized by an X-ray powder diffraction pattern having peaks at: 4.3°, 6.0°, 8.6°, 11.4° and 12.2°±0.2° 2θ.

6. The crystalline form of Febuxostat according to claim 5, further characterized by data selected from one or more of the following: an X-ray powder diffraction pattern substantially as depicted in FIG. 28; additional XRPD peaks at 17.1° and 25.4°±0.2° 2θ; and combinations thereof.

7. A crystalline form of Febuxostat, designated Form F14, characterized by an X-ray powder diffraction pattern having peaks at: 3.2°, 5.1°, 7.0°, 11.8° and 25.5°±0.2° 2θ.

8. The crystalline form of Febuxostat according to claim 7, further characterized by an X-ray powder diffraction pattern substantially as depicted in FIG. 31.

9. A pharmaceutical composition comprising the Febuxostat crystalline form of claim 1 and at least one pharmaceutically acceptable excipient.

10. A pharmaceutical composition comprising the Febuxostat crystalline form of claim 3 and at least one pharmaceutically acceptable excipient.

11. A pharmaceutical composition comprising the Febuxostat crystalline form of claim 5 and at least one pharmaceutically acceptable excipient.

12. A pharmaceutical composition comprising the Febuxostat crystalline form of claim 7 and at least one pharmaceutically acceptable excipient.

13. A process for preparing a pharmaceutical composition comprising combining the Febuxostat crystalline form according to claim 1 with at least one pharmaceutically acceptable excipient.

14. A process for preparing a pharmaceutical composition comprising combining the Febuxostat crystalline form according to claim 3 with at least one pharmaceutically acceptable excipient.

15. A process for preparing a pharmaceutical composition comprising combining the Febuxostat crystalline form according to claim 5 with at least one pharmaceutically acceptable excipient.

16. A process for preparing a pharmaceutical composition comprising combining the Febuxostat crystalline form according to claim 7 with at least one pharmaceutically acceptable excipient.

17. A method of treating a patient with gout, comprising administering to said patient an effective amount of the pharmaceutical composition of claim 9.

18. A method of treating a patient with gout, comprising administering to said patient an effective amount of the pharmaceutical composition of claim 10.

19. A method of treating a patient with gout, comprising administering to said patient an effective amount of the pharmaceutical composition of claim 11.

20. A method of treating a patient with gout, comprising administering to said patient an effective amount of the pharmaceutical composition of claim 12.

* * * * *